US011197919B2

(12) United States Patent
Priceman et al.

(10) Patent No.: US 11,197,919 B2
(45) Date of Patent: Dec. 14, 2021

(54) CHIMERIC ANTIGEN RECEPTORS TARGETING HER2

(71) Applicant: City of Hope, Duarte, CA (US)

(72) Inventors: Saul J. Priceman, Duarte, CA (US); Stephen J. Forman, Duarte, CA (US); Christine E. Brown, Duarte, CA (US)

(73) Assignee: City of Hope, Duarte, CA (US)

( * ) Notice: Subject to any disclaimer, the term of this patent is extended or adjusted under 35 U.S.C. 154(b) by 7 days.

(21) Appl. No.: 15/773,754

(22) PCT Filed: Nov. 4, 2016

(86) PCT No.: PCT/US2016/060724
§ 371 (c)(1),
(2) Date: May 4, 2018

(87) PCT Pub. No.: WO2017/079694
PCT Pub. Date: May 11, 2017

(65) Prior Publication Data
US 2018/0326032 A1    Nov. 15, 2018

Related U.S. Application Data

(60) Provisional application No. 62/251,052, filed on Nov. 4, 2015.

(51) Int. Cl.
| A61K 35/17 | (2015.01) |
| A61P 35/00 | (2006.01) |
| C07K 16/32 | (2006.01) |
| A61K 39/00 | (2006.01) |
| C07K 14/725 | (2006.01) |
| C07K 14/705 | (2006.01) |
| C12N 15/86 | (2006.01) |
| C07K 14/71 | (2006.01) |
| C12N 5/0783 | (2010.01) |
| C07K 16/28 | (2006.01) |

(52) U.S. Cl.
CPC ...... *A61K 39/001106* (2018.08); *A61P 35/00* (2018.01); *C07K 14/7051* (2013.01); *C07K 14/70503* (2013.01); *C07K 14/70521* (2013.01); *C07K 14/71* (2013.01); *C07K 16/2863* (2013.01); *C07K 16/32* (2013.01); *C12N 5/0636* (2013.01); *C12N 15/86* (2013.01); *A61K 35/17* (2013.01); *A61K 2039/505* (2013.01); *A61K 2039/5156* (2013.01); *A61K 2039/5158* (2013.01); *C07K 2317/524* (2013.01); *C07K 2317/622* (2013.01); *C07K 2317/71* (2013.01); *C07K 2319/03* (2013.01); *C07K 2319/33* (2013.01); *C12N 2740/16043* (2013.01); *C12N 2830/15* (2013.01)

(58) Field of Classification Search
CPC ............ A61K 35/17; A61K 39/001106; A61K 2039/505; A61P 35/00; C07K 16/32; C07K 16/2863; C07K 2317/622; C07K 2319/33; C12N 5/0636; C12N 2510/00
See application file for complete search history.

(56) References Cited

U.S. PATENT DOCUMENTS

| 2009/0252729 | A1 | 10/2009 | Farrington et al. | |
| 2011/0136173 | A1 | 6/2011 | Pluckthun et al. | |
| 2011/0294987 | A1 | 12/2011 | Kanazaki et al. | |
| 2012/0301447 | A1 | 11/2012 | Jensen | |
| 2013/0157961 | A1* | 6/2013 | Alila ...................... | A61P 35/02 514/19.6 |
| 2013/0295116 | A1* | 11/2013 | Zahn ...................... | A61P 11/06 424/172.1 |
| 2014/0099309 | A1 | 4/2014 | Powell et al. | |
| 2014/0140976 | A1 | 5/2014 | Rosenblum et al. | |
| 2014/0271582 | A1* | 9/2014 | Forman .............. | C07K 14/7051 424/93.21 |
| 2015/0306141 | A1 | 10/2015 | Jensen | |

FOREIGN PATENT DOCUMENTS

| JP | 2013-531474 | | 8/2013 |
| JP | 2014-510108 | | 4/2014 |
| RU | 2361880 | | 7/2009 |
| WO | WO 2011/137245 | | 11/2011 |
| WO | WO 2012/050374 | | 4/2012 |
| WO | WO 14/031687 | * | 2/2014 |
| WO | WO 2014/070957 | | 5/2014 |
| WO | WO 14/100385 | * | 6/2014 |
| WO | WO 2014/100385 | | 6/2014 |
| WO | WO 2015/028444 | | 3/2015 |
| WO | WO 2015/105522 | | 7/2015 |
| WO | WO 2015/164594 | | 10/2015 |

OTHER PUBLICATIONS

Morgan et al, Mol. Therapy 18(4): 843-851, 2010.*
Jonnalagadda et al, J. ImmunoTherapy of Cancer 1(Suppl 1): p. 18; Nov. 7, 2013, poster abstract.*
Ahmed et al., "Supplementary Data: HER2-specific T cells target primary glioblastoma stem cells and induce regression of autologous experimental tumors," Clin Cancer Res., Jan. 15, 2010, 16(2):474-485.
Ahmed et al., "Regression of experimental medulloblastoma following transfer of HER2-specific T cells,"Cancer Res., Jun. 15, 2007, 67(12):5957-5964.
Edelman et al., "The covalent structure of an entire gammaG immunoglobulin molecule," Proc Natl Acad Sci USA, May 1969 63(1):78-85.
International Search Report in International Application No. PCT/US2016/060724, dated May 18, 2017, 19 pages.

(Continued)

*Primary Examiner* — Kevin K Hill
(74) *Attorney, Agent, or Firm* — Fish & Richardson P.C.

(57) ABSTRACT

Chimeric transmembrane immunoreceptors (CAR) which include an extracellular domain targeted to HER2, a transmembrane region, a costimulatory domain and an intracellular signaling domain are described.

60 Claims, 18 Drawing Sheets

Specification includes a Sequence Listing.

(56) References Cited

OTHER PUBLICATIONS

International Preliminary Report on Patentability in International Application No. PCT/US2016/060724, dated May 8, 2018, 13 pages.

Maus et al., "Antibody-modified T cells: CARs take the front seat for hematologic malignancies," Blood, Apr. 24, 2014 123(17):2625-2635.

Priceman et al., "Smart CARs Engineered for Cancer Immunotherapy," 2015 Curr Opin Oncol., Nov. 2015, 27(6):466-474.

Tobias Riet, "Erhöhung der Antigen-Selektivität von T-Zellen durch Koexpression chimärer Antigen-Rezeptoren unterschiedlicher Spezifität," Nov. 24, 2010, 204 pages, English Abstract.

Zhao et al., "A Herceptin-Based Chimeric Antigen Receptor with Modified Signaling Domains Leads to Enhanced Survival of Transduced T Lymphocytes and Antitumor Activity," J Immunol., Nov. 1, 2009, 183(9):5563-5574.

European Office Action in European Application No. 16863128.1, dated Sep. 16, 2020, 6 pages.

Japanese Office Action in Japanese Application No. 2018-543279, dated Sep. 16, 2020, 9 pages.

Priceman et al., "Regional Delivery of Chimeric Antigen Receptor-Engineered T Cells Effectively Targets HER2 + Breast Cancer Metastasis to the Brain," Clin Cancer Res., Jan. 2018, 24(1):95-105.

Jonnalagadda et al., "Chimeric Antigen Receptors With Mutated IgG4 Fc Spacer Avoid Fc Receptor Binding and Improve T Cell Persistence and Antitumor Efficacy," Mol Ther., Feb. 17, 2015, 23(4):757-768.

Ahmed et al., "HER2-Specific T Cells Target Primary Glioblastoma Stem Cells and Induce Regression of Autologous Experimental Tumors," Clin Canc Res., Jan. 2010, 16(2):474-485.

Brazilian Office Action in Brazilian Application No. BR112018009129, dated Mar. 15, 2021, 5 pages.

Jonnalagadda et al., "Chimeric antigen receptors (CARs) incorporating mutations in the IgG4 Fc spacer region to eliminate Fc receptor recognition results in improved CAR T cell persistence and anti-tumor efficacy," Journal for ImmunoTherapy of Cancer, 2013, 1(Suppl 1):P18.

* cited by examiner

Her2scFv-IgG4(S228P,L235E, N297Q)-CD28tm-CD28gg-Zeta-T2A-CD19t

MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQG
TKVEIKGSTSGSGGSGGGSGGGSSEVQLVESGGGLVQPGGSLRLSCAASGFNIKDTYIHWVRQAPGKGLEWVARIYPTNGYTRYADSVKGRFTISADTSKNTAYLQMNSLRAEDTAVY
YCSRWGGDGFYAMDYWGQGTLVTVSSESKYGPPPPCPAPEFEGGPSVFLFPPKPKDTLMISRTPEVTCVVVDVSQEDPEVQFNWYVDGVEVHNAKTKPREEQFQSTYRVVSVLTVL
HQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSV
MHEALHNHYTQKSLSLSLGKMFWVLVVVGGVLACYSLLVTVAFIIFWVRSKRSGGHSDYMNMTPRRPGPTRKHYQPYAPPRDFAAYRSGGGRVKFSRSADAPAYQQGQNQLYNEL
NLGRREEYDVLDKRRGRDPEMGGKPRRKNPQEGLYNELQKDKMAEAYSEIGMKGERRRGKGHDGLYQGLSTATKDTYDALHMQALPPRLEGGEGRGSLLTCGDVEENPGPRMPP
PRLLFFLLFLLTPMEVRPEEPLVVKVEEGDNAVLQCLKGTSDGPTQQLTWSRESPLKPFLKLSLGLPGLGIHMRPLAIWLFIFNVSQQMGGFYLCQPGPPSEKAWQPGWTVNVEGSGELF
RWNVSDLGGLGCGLKNRSSEGPSSPSGKLMSPKLYVWAKDRPEIWEGEPPCVPPRDSLNQSLSQDLTMAPGSTLWLSCGVPPDSVSRGPLSWTHVHPKGPKSLLSLELKDDRPARDM
WVMETGLLLPRATAQDAGKYYCHRGNLTMSFHLEITARPVLWHWLLRTGGWKVSAVTLAYLIFCLCSLVGILHLQRALVLRRKR

GMCSFRa signal peptide
Her

Her2scFv-IgG4(S228P,L235E,N297Q)-CD8tm-41BB-Zeta-T2A-CD19t

<u>MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGSGGSGGGSGGGSSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSESKYGPP</u>CP<u>APEFEGGPSVFLFPPKPKDTLMISRTPEV
TCVVVDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSVMHEALHNHYTQKSLSLSLGKIYIWAPLAGTCGVLL
SLVITKRGRKKLLYIFKQPFMRPVQTTQEEDGCSCRFPEEEEGGCELGGGRVKFSRSADAPAYQQGQNQLYNELNLGRREEYDVLDKRRGRDPEMGGKPRR</u>
KNPQEGLYNELQKDKMAEAYSEIGMKGERRRGKGHDGLYQGLSTATKDTYDALHMQALPPRLEGGGEGRGSLLTCGDVEENPGPRMPPPRLLFLLLFLLTP
MEVRPEEPLVVKVEEGDNAVLQCLKGTSDGPTQQLTWSRESPLKPFLKSLGLPGLGIHMRPLAIWLFIFNVSQQMGGFYLCQPGPPSEKAWQPGWTVNV
EGSGELFRWNVSDLGGLGCGLKNRSSEGPSSPSGKLMSPKLYVWAKDRPEIWEGEPPCVPPRDSLNQSLSQDLTMAPGSTLWLSCGVPPDSVSRGPLSWT
HVHPKGPKSLLSLELKDDRPARDMWVMETGLLLPRATAQDAGKYYCHRGNLTMSFHLEITARPVLWHWLLRTGGWKVSAVTLAYLIFCLCSLVGILHLQRA
<u>LVLRRKR</u>

<u>GMCSFRa signal peptide</u>
<u>Her2scFv</u>
<u>IgG4(SmP)</u>
CD8 transmembrane
4-1BB cyto
(Gly)3
<u>Zeta</u>
T2A
CD19t

FIG. 2

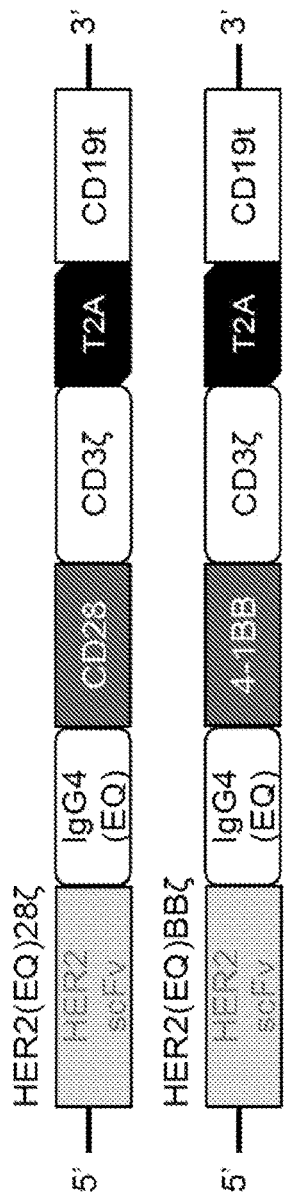
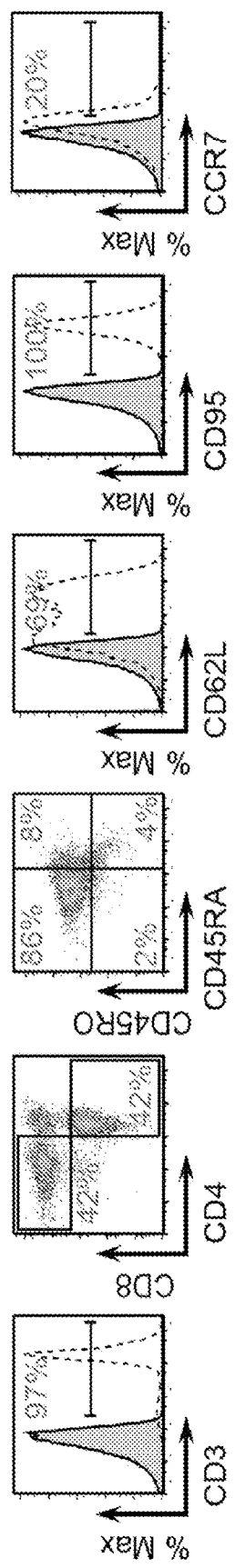
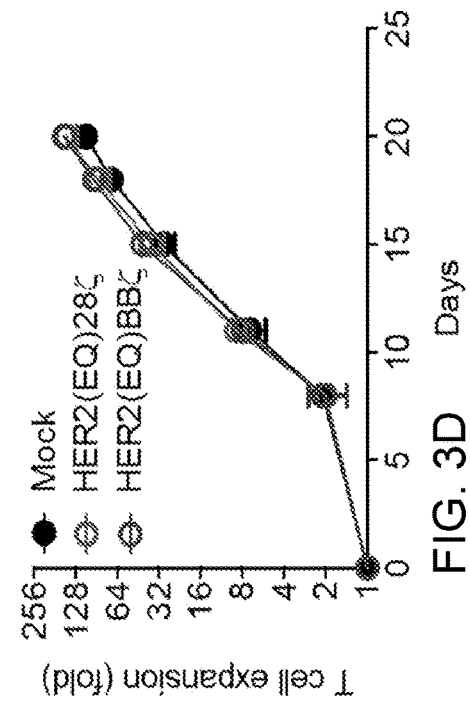
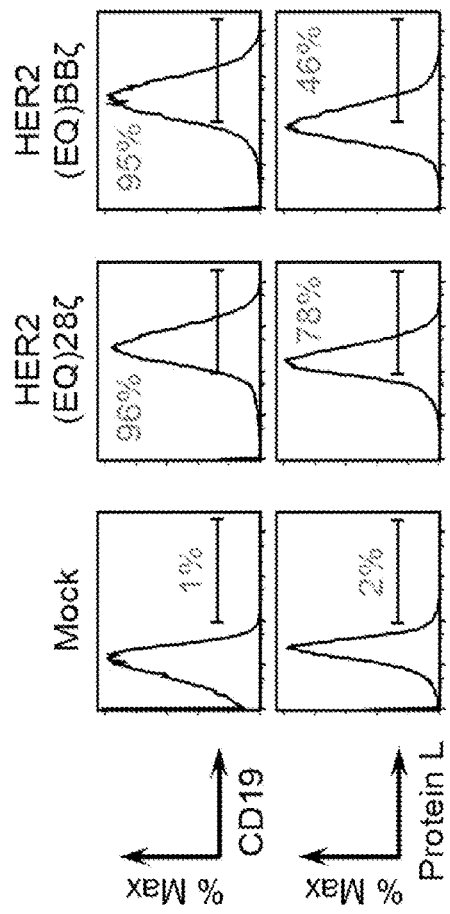
FIG. 3A
FIG. 3B
FIG. 3C
FIG. 3D

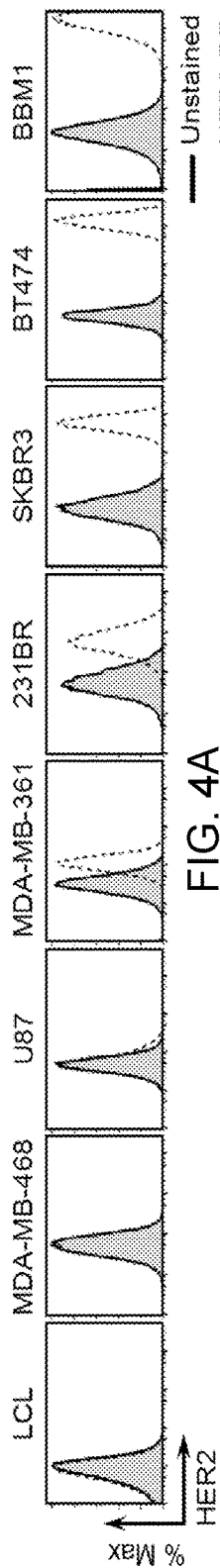
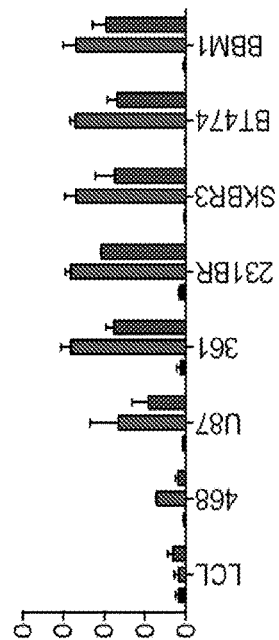
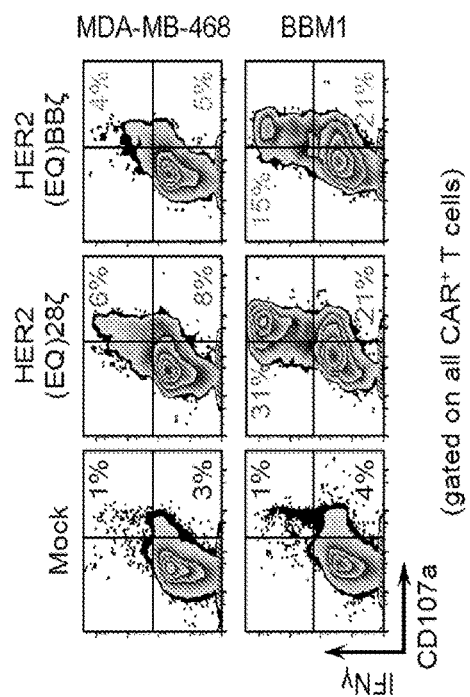
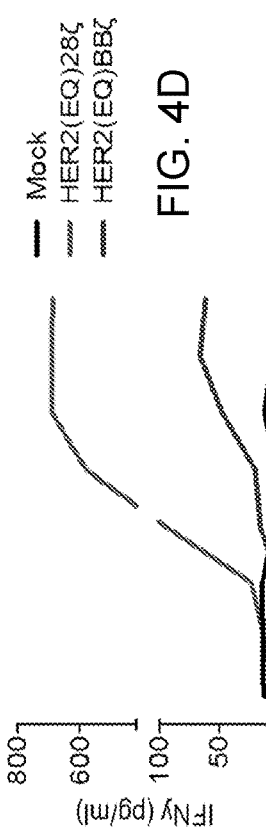
FIG. 4A
FIG. 4B
FIG. 4C
FIG. 4D

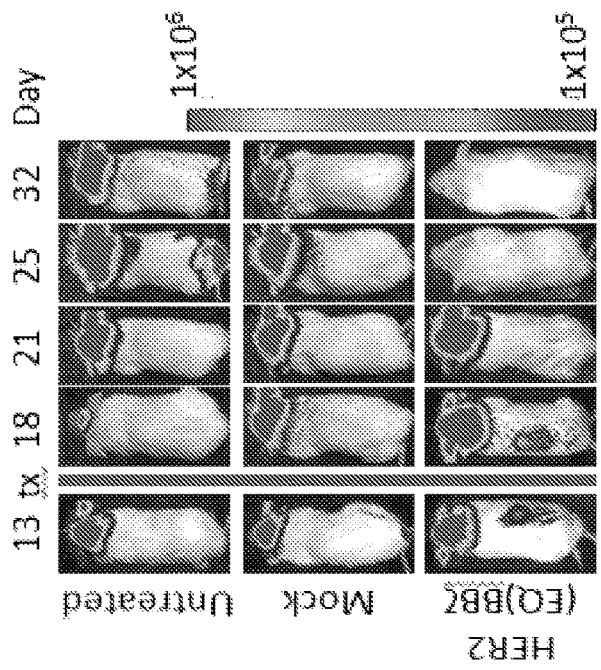
FIG. 8A
FIG. 8B
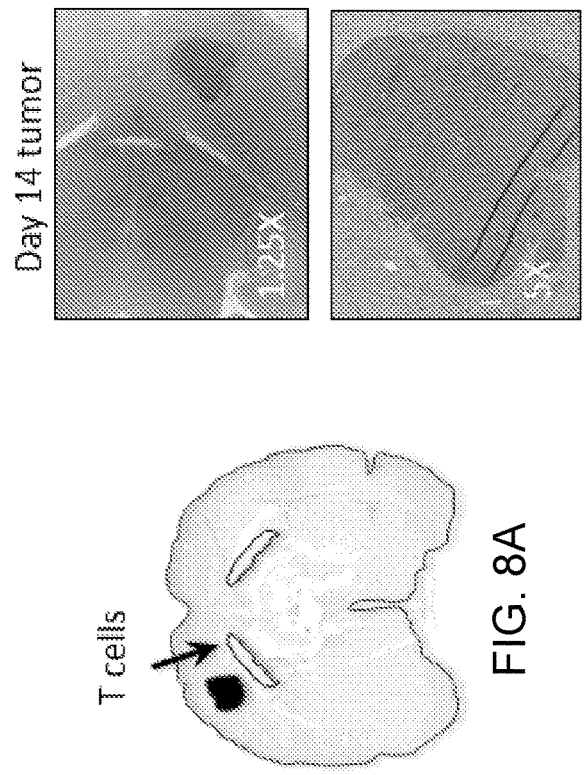
FIG. 8C
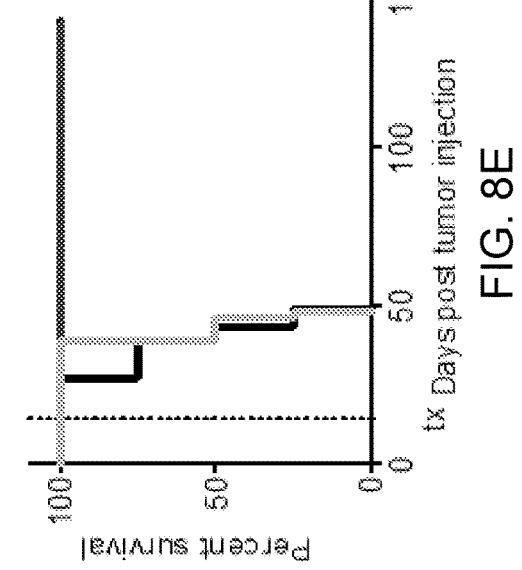
FIG. 8D
FIG. 8E

Her2scFv-CD8hinge-CD8tm-41BB-Zeta-T2A-CD19t

MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGSGGSGGGSGGGSSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSAKPTTTPAPRPPTPAPTIASQPLSLRPEACRPAAGGAVHTR
GLDFACDIYIWAPLAGTCGVLLLSLVITGGGKRGRKKLLYIFKQPFMRPVQTTQEEDGCSCRFPEEEEGGCELGGGRVKFSRSADAPAYQQGQNQLYNELNL
GRREEYDVLDKRRGRDPEMGGKPRRKNPQEGLYNELQKDKMAEAYSEIGMKGERRRGKGHDGLYQGLSTATKDTYDALHMQALPPRLEGGGEGRGSLLT
CGDVEENPGPRMPPPRRLLFFLLFLTPMEVRPEEPLVVKVEEGDNAVLQCLKGTSDGPTQQLTWSRESPLKPFLKSLGLPGLGIHMRPLAIWLFIFNVSQQM
GGFYLCQPGPPSEKAWQPGWTVNVEGSGELFRWNVSDLGGLGCGLKNRSSEGPSSPSGKLMSPKLYVWAKDRPEIWEGEPPCVPPRDSLNQSLSQDLTM
APGSTLWLSCGVPPDSVSRGPLSWTHVHPKGPKSLLSLELKDDRPARDMWVMETGLLLPRATAQDAGKYYCHRGNLTMSFHLEITARPVLWHWLLRTGG
WKVSAVTLAYLIFCLCSLVGILHLQRALVLRRKR

<u>GMCSFRa signal peptide</u>
<u>Her2scFv</u>
<u>CD8 hinge</u>
CD8 transmembrane
<u>(Gly)3</u>
4-1BB cyto
<u>(Gly)3</u>
Zeta
<u>T2A</u>
<u>CD19t</u>

FIG. 9

Her2scFv-Hinge-Linker-CD8tm-41BB-Zeta-T2A-CD19t

<u>MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGGGSGGGSGGGSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSESKYGPPCPPCPGGSSGGGSGIYIWAPLAGTCGVLLLSLV</u>
<u>ITKRGRKKLLYIFKQPFMRPVQTTQEEDGCSCRFPEEEEGGCELGGGRVKFSRSADAPAYQQGQNQLYNELNLGRREEYDVLDKRRGRDPEMGGKPRRKNP</u>
QEGLYNELQKDKMAEAYSEIGMKGERRRGKGHDGLYQGLSTATKDTYDALHMQALPPREGGEGGRGSLLTCGDVEENPGPRLMPPPRLLFLLFLTPMEV
RPEEPLVVKVEEGDNAVLQCLKGTSDGPTQQLTWSRESPLKPFLKLSLGLPGLGIHMRPLAIWLFIFNVSQQMGGFYLCQPGPPSEKAWQPGWTVNVEGS
GELFRWNVSDLGLGCGLKNRSSEGPSSPSGKLMSPKLYVWAKDRPEIWEGEPPCVPPRDSLNQSLSQDLTMAPGSTLWLSCGVPPDSVSRGPLSWTHVH
PKGPKSLLSLELKDDRPARDMWVMETGLLLPRATAQDAGKYYCHRGNLTMSFHLEITARPVLWHWLLRTGGWKVSAVTLAYLIFCLCSLVGILHLQRALVLR
RKR

<u>GMCSFRa signal peptide</u>
<u>Her2scFv</u>
<u>IgG4Hinge</u>
Linker
<u>CD8 transmembrane</u>
4-1BB cyto
(Gly)3
Zeta
<u>T2A</u>
<u>CD19t</u>

FIG. 10

Her2scFv-IgG4(HL-CH3)-CD8tm-41BB-Zeta-T2A-CD19t

MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGGGSGGGSGGGSSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSESKYGPPCPPCPGGGSSGGSGGQPREPQVYTLPPSQEE
MTKNQVSLTCLVKGFYPSDIAVEWESNGQPENNYKTTPPVLDSDGSFFLYSRLTVDKSRWQEGNVFSCSVMHEALHNHYTQKSLSLSLGKIYIWAPLAGTCG
VLLLSLVITLYCNHRNRRRVCKCPRPVVKSGDKPSLSVSTAAEVQLSLNQVQQLSRGHDGLYQGLSTATKDTYDALHMQALPPRLEGGEGRGSLLTCGDVEENPGPRMPPPRLLFFLL
PRRKNPQEGLYNELQKDKMAEAYSEIGMKGERRRGKGHDGLYQGLSTATKDTYDALHMQALPPRLEGGEGRGSLLTCGDVEENPGPRMPPPRLLFFLL
LTPMEVRPEEPLVVKVEEGDNAVLQCLKGTSDGPTQQLTWSRESPLKPFLKLSLGLPGLGIHMRPLAIWLFIFNVSQQMGGFYLCQPGPPSEKAWQPGWT
VNVEGGSELFRWNVSDLGGLGCGLKNRSSEGPSPSGKLMSPKLYVWAKDRPEIWEGEPPCVPPRDSLNQSLSQDLTMAPGSTLWLSCGVPPDSVSRGPL
SWTHVHPKGPKSLLSLELKDDRPARDMWVMETGLLLPRATAQDAGKYYCHRGNLTMSFHLEITARPVLWHWLLRTGGWKVSAVTLAYLIFCLCSLVGILHL
QRALVLRRKR

GMCSFRa signal peptide
Her2scFv
IgG4(SmP)-Hinge
Linker
IgG4-CH3
CD8 transmembrane
4-1BB cyto
(Gly)3
Zeta
T2A
CD19t

FIG. 11

Her2scFv-IgG4(HL-CH3)-CD28tm-CD28gg-Zeta-T2A-CD19t

<u>MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGGGSGGGSGGGSSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS</u>ESKYGPPCPPCPGGGSSGGGSGGGQPREPQVYTLPPSQEE
MTKNQVSLTCLVKGFYPSDIAVEWESNGQPENNYKTTPPVLDSDGSFFLYSRLTVDKSRWQEGNVFSCSVMHEALHNHYTQKSLSLSLGKMFWVLVVVGG
VLACYSLLVTVAFIIFWVRSKRSRGGHSDYMNMTPRRPGPTRKHYQPYAPPRDFAAYRSGGGRVKFSRSADAPAYQQGQNQLYNELNLGRREEYDVLDKR
RGRDPEMGGKPRRKNPQEGLYNELQKDKMAEAYSEIGMKGERRRGKGHDGLYQGLSTATKDTYDALHMQALPPRLEGGGEGRGSLLTCGDVEENPGPR
MPPPRLLFLLLFLTPMEVRPEEPLVVKVEEGDNAVLQCLKGTSDGPTQQLTWSRESPLKPFLKLSLGLPGLGIHMRPLAIWLFIFNVSQQMGGFYLCQPGPPS
EKAWQPGWTVNVEGSGELFRWNVSDLGGLGCGLKNRSSEGPSSPSGKLMSPKLYVWAKDRPEIWEGEPPCVPPRDSLNQSLSQDLTMAPGSTLWLSCG
VPPDSVSRGPLSWTHVHPKGPKSLLSLELKDDRPARDMWWMETGLLPRATAQDAGKYYCHRGNLTMSFHLEITARPVLWHWLLRTGGWKVSAVTLAYLI
<u>FCLCSLVGILHLQRALVLRRKR</u>

<u>GMCSFRa signal peptide</u>
Her2scFv
<u>IgG4(SmP)-Hinge</u>
Linker
<u>IgG4-CH3</u>
CD28 transmembrane
CD28cyto (LLmGG)
(Gly)3
<u>Zeta</u>
T2A
<u>CD19t</u>

FIG. 12

Her2scFv-Linker-CD28tm-CD28gg-Zeta-T2A-CD19t

MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGGGSGGGGSGGGGSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSGGGGSGGGGSGMFWVLVVVGGVLACYSLLVTVAFIIFWVR
SKRSRGGHSDYMNMTPRRPGPTRKHYQPYAPPRDFAAYRSGGGRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPRLEGGGEGRGSLLTCGDVEENPGPRMPPPRLLFFLLFLTPMEVR
PEEPLVVKVEEGDNAVLQCLKGTSDGPTQQLTWSRESPLKPFLKLSLGLPGLGIHMRPLAIWLFIFNVSQQMGGFYLCQPGPPSEKAWQPGWTVNVEGSG
ELFRWNVSDLGGLGGCGLKNRSSEGPSSPSGKLMSPKLYVWAKDRPEIWEGEPPCVPPRDSLNQSLSQDLTMAPGSTLWLSCGVPPDSVSRGPLSWTHVHP
KGPKSLLSLELKDDRPARDMWVMETGLLLPRATAQDAGKYYCHRGNLTMSFHLEITARPVLWHWLLRTGGWKVSAVTLAYLIFCLCSLVGILHLQRALVLRR
KR

GMCSFRa signal peptide
Her2scFv
Linker
CD28 transmembrane
CD28cyto (LLmGG)
(Gly)3
Zeta
T2A
CD19t

FIG. 13

Her2scFv-Linker-CD8tm-41BB-Zeta-T2A-CD19t

MLLLVTSLLLCELPHPAFLLIPDIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGQGTKVEIKGSTSGGGSGGGSGGGSSEVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSSGGGGSGGGGSGIYIWAPLAGTCGVLLLSLVITKRGRKKLLYIF
KQPFMRPVQTTQEEDGCSCRFPEEEEGGCELGGGRVKFSRSADAPAYQQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPRLEGGGEGRGSLLTCGDVEENPGPRMPPPRLLFLFLTPMEVRPEEPLVVKVEE
GDNAVLQCLKGTSDGPTQQLTWSRESPLKPFLKLSLGLPGLGIHMRPLAIWLFIFNVSQQMGGFYLCQPGPPSEKAWQPGWTVNVEGSGELFRWNVSDL
GGLGCGLIKNRSSEGPSSPSGKLMSPKLYVWAKDRPEIWEGEPPCVPPRDSLNQSLSQDLTMAPGSTLWLSCGVPPDSVSRGPLSWTHVHPKGPKSLLSLEL
KDDRPARDMWVMETGILLPRATAQDAGKYYCHRGNLTMSFHLEITARPVLWHWLLRTGGWKVSAVTLAYLIFCLCSLVGILHLQRALVLRRKR

GMCSFRa signal peptide
Her2scFv
Linker
CD8 transmembrane
4-1BB cyto
(Gly)3
Zeta
T2A
CD19t

FIG. 14

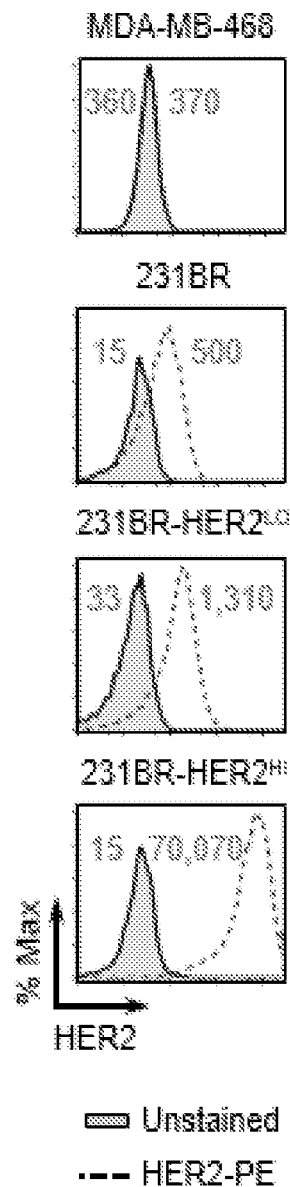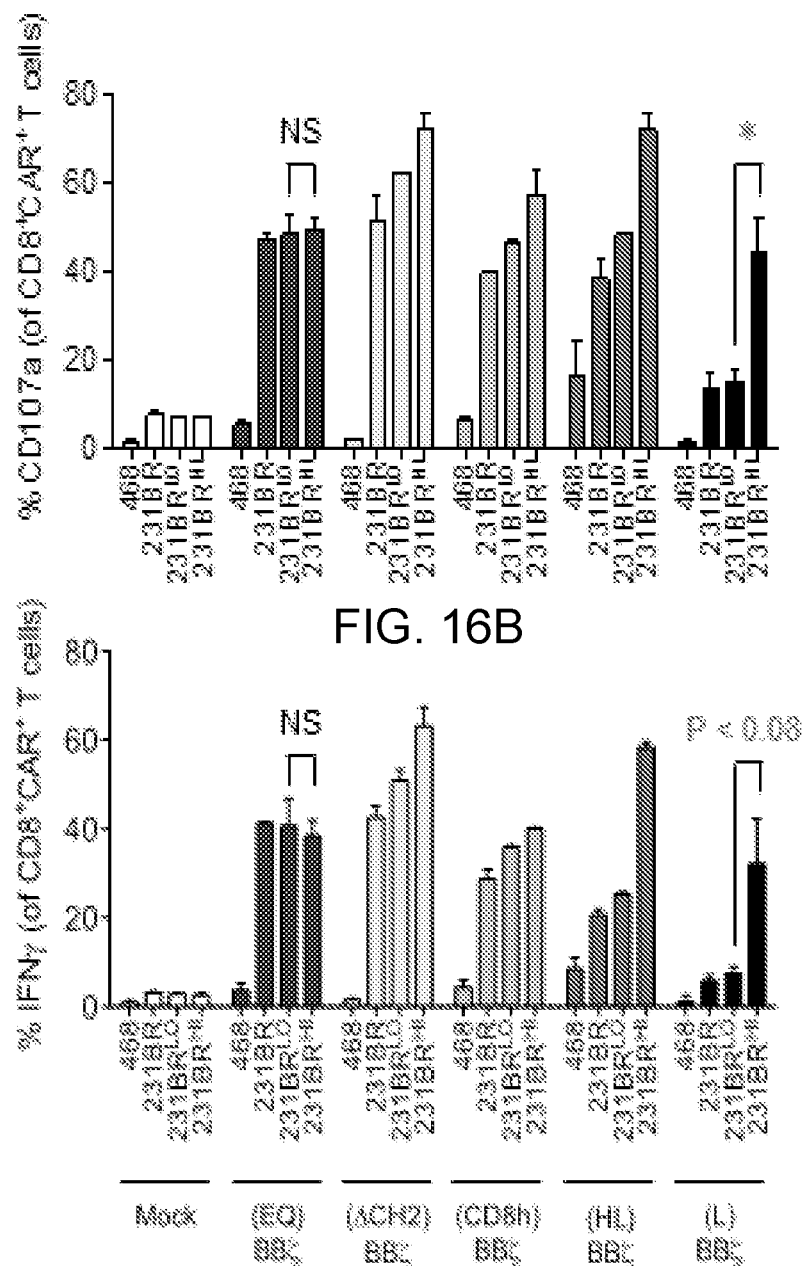
FIG. 16A
FIG. 16B
FIG. 16C

SEQUENCE LISTING

```
<160> NUMBER OF SEQ ID NOS: 42

<210> SEQ ID NO 1
<211> LENGTH: 245
<212> TYPE: PRT
<213> ORGANISM: Homo sapiens
<220> FEATURE:
<221> NAME/KEY: VARIANT
<222> LOCATION: (1)..(245)
<223> OTHER INFORMATION: scEv targeted to HER2

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160
```

```
Trp Val Arg Gln Ala Pro Gly Lys Gly Leu Glu Trp Val Ala Arg Ile
                165                 170                 175
Tyr Pro Thr Asn Gly Tyr Thr Arg Tyr Ala Asp Ser Val Lys Gly Arg
                180                 185                 190
Phe Thr Ile Ser Ala Asp Thr Ser Lys Asn Thr Ala Tyr Leu Gln Met
            195                 200                 205
Asn Ser Leu Arg Ala Glu Asp Thr Ala Val Tyr Tyr Cys Ser Arg Trp
        210                 215                 220
Gly Gly Asp Gly Phe Tyr Ala Met Asp Tyr Trp Gly Gln Gly Thr Leu
225                 230                 235                 240
Val Thr Val Ser Ser
                245

<210> SEQ ID NO 2
<211> LENGTH: 10
<212> TYPE: PRT
<213> ORGANISM: Artificial Sequence
<220> FEATURE:
<223> OTHER INFORMATION: Linker

<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: mutated IgG4 hinge region

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Homo sapiens
<220> FEATURE:
<221> NAME/KEY: VARIANT
<222> LOCATION: (1)..(12)

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Artificial Sequence
<220> FEATURE:
<223> OTHER INFORMATION: chimeric IgG4 mutated hinge and linker

<400> SEQUENCE: 5

Glu Ser Lys Tyr Gly Pro Pro Cys Pro Cys Pro Gly Gly Gly Ser
1               5                   10                  15

Ser Gly Gly Gly Ser Gly
                20

<210> SEQ ID NO 6
<211> LENGTH: 39
<212> TYPE: PRT
```

<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 9
<211> LENGTH: 129
<212> TYPE: PRT
<213> ORGANISM: Artificial Sequence
<220> FEATURE:
<223> OTHER INFORMATION: chimeric IgG4 hinge +

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
            35                  40                  45

Cys Leu Val Lys Gly Phe Tyr Pro Ser Asp Ile Ala Val Glu Trp Glu
            50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly

-continued

```
                115             120             125
Lys

<210> SEQ ID NO 10
<211> LENGTH: 228
<212> TYPE: PRT
<213> ORGANISM: Artificial Sequence
<220> FEATURE:
<223> OTHER INFORMATION: mutated IgG4

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: mutated IgG4

<400> SEQUENCE: 11

Glu Ser Lys Tyr Gly Pro Pro Cys Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
            50                  55                  60
Glu Val His Asn Ala Lys Thr Lys Pro Arg Glu Glu Gln Phe Gln Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
  1               5                  10                  15

Glu Met Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

<400> SEQUENCE: 13

Leu Cys Tyr Leu Leu Asp Gly Ile Leu Phe Ile Tyr Gly Val Ile Leu
  1               5                  10                  15

Thr Ala Leu Phe Leu
             20
```

```
<210> SEQ ID NO 14
<211> LENGTH: 27
<212> TYPE: PRT
<213> ORGANISM: Homo sapiens

<400> SEQUENCE: 14

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Homo sapiens

<400> SEQUENCE: 15

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Homo sapiens

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Homo sapiens

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Homo sapiens

<400> SEQUENCE: 19

Ile Tyr Ile Trp Ala Pro Leu Ala Gly Thr Cys Gly Val Leu Leu Leu
1               5                   10                  15
```

Ser Leu Val Ile Thr Leu Tyr Cys
            20

<210> SEQ ID NO 20
<211> LENGTH: 28
<212> TYPE: PRT
<213> ORGANISM: Homo sapiens

<400> SEQUENCE: 20

Ile Ile Ser Phe Phe Leu Ala Leu Thr Ser Thr Ala Leu Leu Leu Phe
1               5                   10                  15

Leu Leu Phe Phe Leu Thr Leu Arg Phe Ser Val Val
            20                  25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Homo sapiens

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Artificial Sequence
<220> FEATURE:
<223> OTHER INFORMATION: mutated human

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40

<210> SEQ ID NO 26
<211> LENGTH: 1027
<212> TYPE: PRT
<213> ORGANISM: Artificial Sequence
<220> FEATURE:
<223> OTHER INFORMATION: human chimeric Her2scFv-IgG4(L235E,
      N297Q)-CD28tm-CD28gg-Zeta-T2A-CD19t

<400> SEQUENCE: 26

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Asp Val Asn Thr Ala Val Ala Trp Tyr Gln Gln Lys Pro Gly Lys
50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
            85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
            115                 120                 125

Lys Gly Ser Thr Ser Gly Gly Gly Ser Gly Gly Gly Ser Gly Gly Gly
            130                 135                 140

Gly Ser Ser Glu Val Gln Leu Val Glu Ser Gly Gly Gly Leu Val Gln
145                 150                 155                 160

-continued

```
Pro Gly Gly Ser Leu Arg Leu Ser Cys Ala Ala Ser Gly Phe Asn Ile
            165                 170                 175
Lys Asp Thr Tyr Ile His Trp Val Arg Gln Ala Pro Gly Lys Gly Leu
        180                 185                 190
Glu Trp Val Ala Arg Ile Tyr Pro Thr Asn Gly Tyr Thr Arg Tyr Ala
    195                 200                 205
Asp Ser Val Lys Gly Arg Phe Thr Ile Ser Ala Asp Thr Ser Lys Asn
210                 215                 220
Thr Ala Tyr Leu Gln Met Asn Ser Leu Arg Ala Glu Asp Thr Ala Val
225                 230                 235                 240
Tyr Tyr Cys Ser Arg Trp Gly Asp Gly Phe Tyr Ala Met Asp Tyr
                245                 250                 255
Trp Gly Gln Gly Thr Leu Val Thr Val Ser Ser Glu Ser Lys Tyr Gly
            260                 265                 270
Pro Pro Cys Pro Pro Cys Pro Ala Pro Glu Phe Glu Gly Gly Pro Ser
        275                 280                 285
Val Phe Leu Phe Pro Pro Lys Pro Lys Asp Thr Leu Met Ile Ser Arg
    290                 295                 300
Thr Pro Glu Val Thr Cys Val Val Asp Val Ser Gln Glu Asp Pro
305                 310                 315                 320
Glu Val Gln Phe Asn Trp Tyr Val Asp Gly Val Glu Val His Asn Ala
                325                 330                 335
Lys Thr Lys Pro Arg Glu Gln Phe Gln Ser Thr Tyr Arg Val Val
            340                 345                 350
Ser Val Leu Thr Val Leu His Gln Asp Trp Leu Asn Gly Lys Glu Tyr
        355                 360                 365
Lys Cys Lys Val Ser Asn Lys Gly Leu Pro Ser Ser Ile Glu Lys Thr
    370                 375                 380
Ile Ser Lys Ala Lys Gly Gln Pro Arg Glu Pro Gln Val Tyr Thr Leu
385                 390                 395                 400
Pro Pro Ser Gln Glu Glu Met Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Arg Leu Thr Val Asp Lys Ser
    450                 455                 460
Arg Trp Gln Glu Gly Asn Val Phe Ser Cys Ser Val Met His Glu Ala
465                 470                 475                 480
Leu His Asn His Tyr Thr Gln Lys Ser Leu Ser Leu Ser Leu Gly Lys
                485                 490                 495
Met Phe Trp Val Leu Val Val Gly Gly Val Leu Ala Cys Tyr Ser
            500                 505                 510
Leu Leu Val Thr Val Ala Phe Ile Ile Phe Trp Val Arg Ser Lys Arg
        515                 520                 525
Ser Arg Gly Gly His Ser Asp Tyr Met Asn Met Thr Pro Arg Arg Pro
    530                 535                 540
Gly Pro Thr Arg Lys His Tyr Gln Pro Tyr Ala Pro Pro Arg Asp Phe
545                 550                 555                 560
Ala Ala Tyr Arg Ser Gly Gly Gly Arg Val Lys Phe Ser Arg Ser Ala
                565                 570                 575
Asp Ala Pro Ala Tyr Gln Gln Gly Gln Asn Gln Leu Tyr Asn Glu Leu
```

-continued

```
                580                 585                 590
Asn Leu Gly Arg Arg Glu Glu Tyr Asp Val Leu Asp Lys Arg Arg Gly
            595                 600                 605
Arg Asp Pro Glu Met Gly Gly Lys Pro Arg Arg Lys Asn Pro Gln Glu
        610                 615                 620
Gly Leu Tyr Asn Glu Leu Gln Lys Asp Lys Met Ala Glu Ala Tyr Ser
625                 630                 635                 640
Glu Ile Gly Met Lys Gly Glu Arg Arg Arg Gly Lys Gly His Asp Gly
                645                 650                 655
Leu Tyr Gln Gly Leu Ser Thr Ala Thr Lys Asp Thr Tyr Asp Ala Leu
            660                 665                 670
His Met Gln Ala Leu Pro Pro Arg Leu Glu Gly Gly Gly Glu Gly Arg
        675                 680                 685
Gly Ser Leu Leu Thr Cys Gly Asp Val Glu Glu Asn Pro Gly Pro Arg
    690                 695                 700
Met Pro Pro Pro Arg Leu Leu Phe Phe Leu Leu Phe Leu Thr Pro Met
705                 710                 715                 720
Glu Val Arg Pro Glu Glu Pro Leu Val Val Lys Val Glu Glu Gly Asp
                725                 730                 735
Asn Ala Val Leu Gln Cys Leu Lys Gly Thr Ser Asp Gly Pro Thr Gln
            740                 745                 750
Gln Leu Thr Trp Ser Arg Glu Ser Pro Leu Lys Pro Phe Leu Lys Leu
        755                 760                 765
Ser Leu Gly Leu Pro Gly Leu Gly Ile His Met Arg Pro Leu Ala Ile
    770                 775                 780
Trp Leu Phe Ile Phe Asn Val Ser Gln Gln Met Gly Gly Phe Tyr Leu
785                 790                 795                 800
Cys Gln Pro Gly Pro Ser Glu Lys Ala Trp Gln Pro Gly Trp Thr
                805                 810                 815
Val Asn Val Glu Gly Ser Gly Glu Leu Phe Arg Trp Asn Val Ser Asp
            820                 825                 830
Leu Gly Gly Leu Gly Cys Gly Leu Lys Asn Arg Ser Ser Glu Gly Pro
        835                 840                 845
Ser Ser Pro Ser Gly Lys Leu Met Ser Pro Lys Leu Tyr Val Trp Ala
    850                 855                 860
Lys Asp Arg Pro Glu Ile Trp Glu Gly Glu Pro Pro Cys Val Pro Pro
865                 870                 875                 880
Arg Asp Ser Leu Asn Gln Ser Leu Ser Gln Asp Leu Thr Met Ala Pro
                885                 890                 895
Gly Ser Thr Leu Trp Leu Ser Cys Gly Val Pro Pro Asp Ser Val Ser
            900                 905                 910
Arg Gly Pro Leu Ser Trp Thr His Val His Pro Lys Gly Pro Lys Ser
        915                 920                 925
Leu Leu Ser Leu Glu Leu Lys Asp Asp Arg Pro Ala Arg Asp Met Trp
    930                 935                 940
Val Met Glu Thr Gly Leu Leu Pro Arg Ala Thr Ala Gln Asp Ala
945                 950                 955                 960
Gly Lys Tyr Tyr Cys His Arg Gly Asn Leu Thr Met Ser Phe His Leu
                965                 970                 975
Glu Ile Thr Ala Arg Pro Val Leu Trp His Trp Leu Leu Arg Thr Gly
            980                 985                 990
Gly Trp Lys Val Ser Ala Val Thr Leu Ala Tyr Leu Ile Phe Cys Leu
        995                 1000                1005
```

```
Cys Ser Leu Val Gly Ile Leu His Leu Gln Arg Ala Leu Val Leu
        1010            1015                1020

Arg Arg Lys Arg
    1025

<210> SEQ ID NO 27
<211> LENGTH: 1021
<212> TYPE: PRT
<213> ORGANISM: Artificial Sequence
<220> FEATURE:
<223> OTHER INFORMATION: human chimeric
      Her2scFv-IgG4(L235E,N297Q)-CD8tm-41BB-Zeta-T2A-CD19t

<400> SEQUENCE: 27

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Gly Gly Ser Gly Gly Gly Ser Gly Gly Gly
130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Glu Ser Lys Tyr Gly
            260                 265                 270

Pro Pro Cys Pro Pro Cys Pro Ala Pro Glu Phe Glu Gly Gly Pro Ser
        275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
```

```
                325                 330                 335
Lys Thr Lys Pro Arg Glu Glu Gln Phe Gln Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Gly Leu Pro Ser Ser Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Arg Leu Thr Val Asp Lys Ser
            450                 455                 460

Arg Trp Gln Glu Gly Asn Val Phe Ser Cys Ser Val Met His Glu Ala
465                 470                 475                 480

Leu His Asn His Tyr Thr Gln Lys Ser Leu Ser Leu Ser Leu Gly Lys
            485                 490                 495

Ile Tyr Ile Trp Ala Pro Leu Ala Gly Thr Cys Gly Val Leu Leu Leu
            500                 505                 510

Ser Leu Val Ile Thr Lys Arg Gly Arg Lys Lys Leu Leu Tyr Ile Phe
            515                 520                 525

Lys Gln Pro Phe Met Arg Pro Val Gln Thr Thr Gln Glu Glu Asp Gly
            530                 535                 540

Cys Ser Cys Arg Phe Pro Glu Glu Glu Gly Gly Cys Glu Leu Gly
545                 550                 555                 560

Gly Gly Arg Val Lys Phe Ser Arg Ser Ala Asp Ala Pro Ala Tyr Gln
            565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
            595                 600                 605

Gly Lys Pro Arg Arg Lys Asn Pro Gln Glu Gly Leu Tyr Asn Glu Leu
            610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
            645                 650                 655

Thr Ala Thr Lys Asp Thr Tyr Asp Ala Leu His Met Gln Ala Leu Pro
            660                 665                 670

Pro Arg Leu Glu Gly Gly Gly Glu Gly Arg Gly Ser Leu Leu Thr Cys
            675                 680                 685

Gly Asp Val Glu Glu Asn Pro Gly Pro Arg Met Pro Pro Arg Leu
690                 695                 700

Leu Phe Phe Leu Leu Phe Leu Thr Pro Met Glu Val Arg Pro Glu Glu
705                 710                 715                 720

Pro Leu Val Val Lys Val Glu Glu Gly Asp Asn Ala Val Leu Gln Cys
            725                 730                 735

Leu Lys Gly Thr Ser Asp Gly Pro Thr Gln Gln Leu Thr Trp Ser Arg
            740                 745                 750
```

-continued

```
Glu Ser Pro Leu Lys Pro Phe Leu Lys Leu Ser Leu Gly Leu Pro Gly
        755                 760                 765

Leu Gly Ile His Met Arg Pro Leu Ala Ile Trp Leu Phe Ile Phe Asn
    770                 775                 780

Val Ser Gln Gln Met Gly Gly Phe Tyr Leu Cys Gln Pro Gly Pro Pro
785                 790                 795                 800

Ser Glu Lys Ala Trp Gln Pro Gly Trp Thr Val Asn Val Glu Gly Ser
                805                 810                 815

Gly Glu Leu Phe Arg Trp Asn Val Ser Asp Leu Gly Gly Leu Gly Cys
            820                 825                 830

Gly Leu Lys Asn Arg Ser Glu Gly Pro Ser Pro Ser Gly Lys
            835                 840                 845

Leu Met Ser Pro Lys Leu Tyr Val Trp Ala Lys Asp Arg Pro Glu Ile
    850                 855                 860

Trp Glu Gly Glu Pro Pro Cys Val Pro Arg Asp Ser Leu Asn Gln
865                 870                 875                 880

Ser Leu Ser Gln Asp Leu Thr Met Ala Pro Gly Ser Thr Leu Trp Leu
                885                 890                 895

Ser Cys Gly Val Pro Pro Asp Ser Val Ser Arg Gly Pro Leu Ser Trp
            900                 905                 910

Thr His Val His Pro Lys Gly Pro Lys Ser Leu Leu Ser Leu Glu Leu
        915                 920                 925

Lys Asp Asp Arg Pro Ala Arg Asp Met Trp Val Met Glu Thr Gly Leu
    930                 935                 940

Leu Leu Pro Arg Ala Thr Ala Gln Asp Ala Gly Lys Tyr Tyr Cys His
945                 950                 955                 960

Arg Gly Asn Leu Thr Met Ser Phe His Leu Glu Ile Thr Ala Arg Pro
                965                 970                 975

Val Leu Trp His Trp Leu Leu Arg Thr Gly Gly Trp Lys Val Ser Ala
            980                 985                 990

Val Thr Leu Ala Tyr Leu Ile Phe  Cys Leu Cys Ser Leu  Val Gly Ile
        995                 1000                1005

Leu His  Leu Gln Arg Ala Leu  Val Leu Arg Arg Lys  Arg
    1010                1015                1020

<210> SEQ ID NO 28
<211> LENGTH: 843
<212> TYPE: PRT
<213> ORGANISM: Artificial Sequence
<220> FEATURE:
<223> OTHER INFORMATION: human chimeric Her2scFv-CD8hinge-CD8tm-41BB-
      Zeta-T2A-CD19t

<400> SEQUENCE: 28

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
```

```
                       85                  90                  95
        Ile Ser Ser Leu Gln Pro Glu Asp Phe Ala Thr Tyr Tyr Cys Gln Gln
                            100                 105                 110

His Tyr Thr Thr Pro Pro Thr Phe Gly Gln Gly Thr Lys Val Glu Ile
                            115                 120                 125

Lys Gly Ser Thr Ser Gly Gly Gly Ser Gly Gly Gly Ser Gly Gly Gly
                130                 135                 140

Gly Ser Ser Glu Val Gln Leu Val Glu Ser Gly Gly Gly Leu Val Gln
        145                 150                 155                 160

Pro Gly Gly Ser Leu Arg Leu Ser Cys Ala Ala Ser Gly Phe Asn Ile
                            165                 170                 175

Lys Asp Thr Tyr Ile His Trp Val Arg Gln Ala Pro Gly Lys Gly Leu
                            180                 185                 190

Glu Trp Val Ala Arg Ile Tyr Pro Thr Asn Gly Tyr Thr Arg Tyr Ala
                            195                 200                 205

Asp Ser Val Lys Gly Arg Phe Thr Ile Ser Ala Asp Thr Ser Lys Asn
                210                 215                 220

Thr Ala Tyr Leu Gln Met Asn Ser Leu Arg Ala Glu Asp Thr Ala Val
        225                 230                 235                 240

Tyr Tyr Cys Ser Arg Trp Gly Gly Asp Gly Phe Tyr Ala Met Asp Tyr
                            245                 250                 255

Trp Gly Gln Gly Thr Leu Val Thr Val Ser Ser Ala Lys Pro Thr Thr
                            260                 265                 270

Thr Pro Ala Pro Arg Pro Pro Thr Pro Ala Pro Thr Ile Ala Ser Gln
                            275                 280                 285

Pro Leu Ser Leu Arg Pro Glu Ala Cys Arg Pro Ala Ala Gly Gly Ala
                290                 295                 300

Val His Thr Arg Gly Leu Asp Phe Ala Cys Asp Ile Tyr Ile Trp Ala
        305                 310                 315                 320

Pro Leu Ala Gly Thr Cys Gly Val Leu Leu Leu Ser Leu Val Ile Thr
                            325                 330                 335

Gly Gly Gly Lys Arg Gly Arg Lys Lys Leu Leu Tyr Ile Phe Lys Gln
                            340                 345                 350

Pro Phe Met Arg Pro Val Gln Thr Thr Gln Glu Glu Asp Gly Cys Ser
                            355                 360                 365

Cys Arg Phe Pro Glu Glu Glu Gly Gly Cys Glu Leu Gly Gly Gly
                370                 375                 380

Arg Val Lys Phe Ser Arg Ser Ala Asp Ala Pro Ala Tyr Gln Gln Gly
        385                 390                 395                 400

Gln Asn Gln Leu Tyr Asn Glu Leu Asn Leu Gly Arg Arg Glu Glu Tyr
                            405                 410                 415

Asp Val Leu Asp Lys Arg Arg Gly Arg Asp Pro Glu Met Gly Gly Lys
                            420                 425                 430

Pro Arg Arg Lys Asn Pro Gln Glu Gly Leu Tyr Asn Glu Leu Gln Lys
                            435                 440                 445

Asp Lys Met Ala Glu Ala Tyr Ser Glu Ile Gly Met Lys Gly Glu Arg
                            450                 455                 460

Arg Arg Gly Lys Gly His Asp Gly Leu Tyr Gln Gly Leu Ser Thr Ala
        465                 470                 475                 480

Thr Lys Asp Thr Tyr Asp Ala Leu His Met Gln Ala Leu Pro Pro Arg
                            485                 490                 495

Leu Glu Gly Gly Gly Glu Gly Arg Gly Ser Leu Leu Thr Cys Gly Asp
                            500                 505                 510
```

Val Glu Glu Asn Pro Gly Pro Arg Met Pro Pro Arg Leu Leu Phe
    515                 520                 525

Phe Leu Leu Phe Leu Thr Pro Met Glu Val Arg Pro Glu Glu Pro Leu
530                 535                 540

Val Val Lys Val Glu Glu Gly Asp Asn Ala Val Leu Gln Cys Leu Lys
545                 550                 555                 560

Gly Thr Ser Asp Gly Pro Thr Gln Gln Leu Thr Trp Ser Arg Glu Ser
                565                 570                 575

Pro Leu Lys Pro Phe Leu Lys Leu Ser Leu Gly Leu Pro Gly Leu Gly
            580                 585                 590

Ile His Met Arg Pro Leu Ala Ile Trp Leu Phe Ile Phe Asn Val Ser
        595                 600                 605

Gln Gln Met Gly Gly Phe Tyr Leu Cys Gln Pro Gly Pro Pro Ser Glu
    610                 615                 620

Lys Ala Trp Gln Pro Gly Trp Thr Val Asn Val Glu Gly Ser Gly Glu
625                 630                 635                 640

Leu Phe Arg Trp Asn Val Ser Asp Leu Gly Gly Leu Gly Cys Gly Leu
                645                 650                 655

Lys Asn Arg Ser Ser Glu Gly Pro Ser Ser Pro Ser Gly Lys Leu Met
            660                 665                 670

Ser Pro Lys Leu Tyr Val Trp Ala Lys Asp Arg Pro Glu Ile Trp Glu
        675                 680                 685

Gly Glu Pro Pro Cys Val Pro Pro Arg Asp Ser Leu Asn Gln Ser Leu
    690                 695                 700

Ser Gln Asp Leu Thr Met Ala Pro Gly Ser Thr Leu Trp Leu Ser Cys
705                 710                 715                 720

Gly Val Pro Pro Asp Ser Val Ser Arg Gly Pro Leu Ser Trp Thr His
                725                 730                 735

Val His Pro Lys Gly Pro Lys Ser Leu Leu Ser Leu Glu Leu Lys Asp
            740                 745                 750

Asp Arg Pro Ala Arg Asp Met Trp Val Met Glu Thr Gly Leu Leu Leu
        755                 760                 765

Pro Arg Ala Thr Ala Gln Asp Ala Gly Lys Tyr Tyr Cys His Arg Gly
    770                 775                 780

Asn Leu Thr Met Ser Phe His Leu Glu Ile Thr Ala Arg Pro Val Leu
785                 790                 795                 800

Trp His Trp Leu Leu Arg Thr Gly Gly Trp Lys Val Ser Ala Val Thr
                805                 810                 815

Leu Ala Tyr Leu Ile Phe Cys Leu Cys Ser Leu Val Gly Ile Leu His
            820                 825                 830

Leu Gln Arg Ala Leu Val Leu Arg Arg Lys Arg
        835                 840

<210> SEQ ID NO 29
<211> LENGTH: 814
<212> TYPE: PRT
<213> ORGANISM: Artificial Sequence
<220> FEATURE:
<223> OTHER INFORMATION: human chimeric Her2scFv-Hinge-Linker-CD8tm-
    41BB-Zeta-T2A-CD19t

<400> SEQUENCE: 29

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser

-continued

```
                20                  25                  30
Leu Ser Ala Ser Val Gly Asp Arg Val Thr Ile Thr Cys Arg Ala Ser
            35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Gly Gly Ser Gly Gly Ser Gly Gly Gly
        130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Glu Ser Lys Tyr Gly
            260                 265                 270

Pro Pro Cys Pro Pro Cys Pro Gly Gly Gly Ser Ser Gly Gly Gly Ser
        275                 280                 285

Gly Ile Tyr Ile Trp Ala Pro Leu Ala Gly Thr Cys Gly Val Leu Leu
    290                 295                 300

Leu Ser Leu Val Ile Thr Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Gly Gly Gly Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445
```

Ser Thr Ala Thr Lys Asp Thr Tyr Asp Ala Leu His Met Gln Ala Leu
            450                 455                 460

Pro Pro Arg Glu Gly Gly Glu Gly Arg Gly Ser Leu Leu Thr Cys
465                 470                 475                 480

Gly Asp Val Glu Glu Asn Pro Gly Pro Arg Leu Met Pro Pro Arg
                485                 490                 495

Leu Leu Phe Phe Leu Leu Phe Leu Thr Pro Met Glu Val Arg Pro Glu
            500                 505                 510

Glu Pro Leu Val Val Lys Val Glu Glu Gly Asp Asn Ala Val Leu Gln
            515                 520                 525

Cys Leu Lys Gly Thr Ser Asp Gly Pro Thr Gln Gln Leu Thr Trp Ser
530                 535                 540

Arg Glu Ser Pro Leu Lys Pro Phe Leu Lys Leu Ser Leu Gly Leu Pro
545                 550                 555                 560

Gly Leu Gly Ile His Met Arg Pro Leu Ala Ile Trp Leu Phe Ile Phe
                565                 570                 575

Asn Val Ser Gln Gln Met Gly Gly Phe Tyr Leu Cys Gln Pro Gly Pro
            580                 585                 590

Pro Ser Glu Lys Ala Trp Gln Pro Gly Trp Thr Val Asn Val Glu Gly
            595                 600                 605

Ser Gly Glu Leu Phe Arg Trp Asn Val Ser Asp Leu Gly Gly Leu Gly
610                 615                 620

Cys Gly Leu Lys Asn Arg Ser Ser Glu Gly Pro Ser Ser Pro Ser Gly
625                 630                 635                 640

Lys Leu Met Ser Pro Lys Leu Tyr Val Trp Ala Lys Asp Arg Pro Glu
                645                 650                 655

Ile Trp Glu Gly Glu Pro Pro Cys Val Pro Arg Asp Ser Leu Asn
                660                 665                 670

Gln Ser Leu Ser Gln Asp Leu Thr Met Ala Pro Gly Ser Thr Leu Trp
            675                 680                 685

Leu Ser Cys Gly Val Pro Pro Asp Ser Val Ser Arg Gly Pro Leu Ser
690                 695                 700

Trp Thr His Val His Pro Lys Gly Pro Lys Ser Leu Leu Ser Leu Glu
705                 710                 715                 720

Leu Lys Asp Asp Arg Pro Ala Arg Asp Met Trp Val Met Glu Thr Gly
                725                 730                 735

Leu Leu Leu Pro Arg Ala Thr Ala Gln Asp Ala Gly Lys Tyr Tyr Cys
            740                 745                 750

His Arg Gly Asn Leu Thr Met Ser Phe His Leu Glu Ile Thr Ala Arg
            755                 760                 765

Pro Val Leu Trp His Trp Leu Leu Arg Thr Gly Gly Trp Lys Val Ser
770                 775                 780

Ala Val Thr Leu Ala Tyr Leu Ile Phe Cys Leu Cys Ser Leu Val Gly
785                 790                 795                 800

Ile Leu His Leu Gln Arg Ala Leu Val Leu Arg Arg Lys Arg
                805                 810

<210> SEQ ID NO 30
<211> LENGTH: 921
<212> TYPE: PRT
<213> ORGANISM: Artificial Sequence
<220> FEATURE:
<223> OTHER INFORMATION: human chimeric Her2scFv-IgG4(HL-CH3)-CD8tm-
      41BB-Zeta-T2A-CD19t

```
<400> SEQUENCE: 30

Met Leu Leu Leu Val Thr Ser Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Asp Val Asn Thr Ala Val Ala Trp Tyr Gln Gln Lys Pro Gly Lys
50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
            115                 120                 125

Lys Gly Ser Thr Ser Gly Gly Gly Ser Gly Gly Gly Ser Gly Gly Gly
            130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
            195                 200                 205

Asp Ser Val Lys Gly Arg Phe Thr Ile Ser Ala Asp Thr Ser Lys Asn
210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Glu Ser Lys Tyr Gly
            260                 265                 270

Pro Pro Cys Pro Pro Cys Pro Gly Gly Gly Ser Gly Gly Gly Gly Ser
            275                 280                 285

Gly Gly Gln Pro Arg Glu Pro Gln Val Tyr Thr Leu Pro Pro Ser Gln
290                 295                 300

Glu Glu Met Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Arg Leu Thr Val Asp Lys Ser Arg Trp Gln Glu
            355                 360                 365

Gly Asn Val Phe Ser Cys Ser Val Met His Glu Ala Leu His Asn His
370                 375                 380

Tyr Thr Gln Lys Ser Leu Ser Leu Ser Leu Gly Lys Ile Tyr Ile Trp
385                 390                 395                 400

Ala Pro Leu Ala Gly Thr Cys Gly Val Leu Leu Leu Ser Leu Val Ile
                405                 410                 415
```

```
Thr Lys Arg Gly Arg Lys Lys Leu Leu Tyr Ile Phe Lys Gln Pro Phe
            420                 425                 430

Met Arg Pro Val Gln Thr Thr Gln Glu Glu Asp Gly Cys Ser Cys Arg
            435                 440                 445

Phe Pro Glu Glu Glu Glu Gly Gly Cys Glu Leu Gly Gly Gly Arg Val
            450                 455                 460

Lys Phe Ser Arg Ser Ala Asp Ala Pro Ala Tyr Gln Gln Gly Gln Asn
465                 470                 475                 480

Gln Leu Tyr Asn Glu Leu Asn Leu Gly Arg Arg Glu Glu Tyr Asp Val
                    485                 490                 495

Leu Asp Lys Arg Arg Gly Arg Asp Pro Glu Met Gly Gly Lys Pro Arg
            500                 505                 510

Arg Lys Asn Pro Gln Glu Gly Leu Tyr Asn Glu Leu Gln Lys Asp Lys
            515                 520                 525

Met Ala Glu Ala Tyr Ser Glu Ile Gly Met Lys Gly Glu Arg Arg Arg
            530                 535                 540

Gly Lys Gly His Asp Gly Leu Tyr Gln Gly Leu Ser Thr Ala Thr Lys
545                 550                 555                 560

Asp Thr Tyr Asp Ala Leu His Met Gln Ala Leu Pro Pro Arg Leu Glu
                    565                 570                 575

Gly Gly Gly Glu Gly Arg Gly Ser Leu Leu Thr Cys Gly Asp Val Glu
            580                 585                 590

Glu Asn Pro Gly Pro Arg Met Pro Pro Arg Leu Leu Phe Phe Leu
            595                 600                 605

Leu Phe Leu Thr Pro Met Glu Val Arg Pro Glu Glu Pro Leu Val Val
            610                 615                 620

Lys Val Glu Glu Gly Asp Asn Ala Val Leu Gln Cys Leu Lys Gly Thr
625                 630                 635                 640

Ser Asp Gly Pro Thr Gln Gln Leu Thr Trp Ser Arg Glu Ser Pro Leu
                    645                 650                 655

Lys Pro Phe Leu Lys Leu Ser Leu Gly Leu Pro Gly Leu Gly Ile His
            660                 665                 670

Met Arg Pro Leu Ala Ile Trp Leu Phe Ile Phe Asn Val Ser Gln Gln
            675                 680                 685

Met Gly Gly Phe Tyr Leu Cys Gln Pro Gly Pro Pro Ser Glu Lys Ala
            690                 695                 700

Trp Gln Pro Gly Trp Thr Val Asn Val Glu Gly Ser Gly Glu Leu Phe
705                 710                 715                 720

Arg Trp Asn Val Ser Asp Leu Gly Gly Leu Gly Cys Gly Leu Lys Asn
                    725                 730                 735

Arg Ser Ser Glu Gly Pro Ser Ser Pro Ser Gly Lys Leu Met Ser Pro
            740                 745                 750

Lys Leu Tyr Val Trp Ala Lys Asp Arg Pro Glu Ile Trp Glu Gly Glu
            755                 760                 765

Pro Pro Cys Val Pro Pro Arg Asp Ser Leu Asn Gln Ser Leu Ser Gln
            770                 775                 780

Asp Leu Thr Met Ala Pro Gly Ser Thr Leu Trp Leu Ser Cys Gly Val
785                 790                 795                 800

Pro Pro Asp Ser Val Ser Arg Gly Pro Leu Ser Trp Thr His Val His
                    805                 810                 815

Pro Lys Gly Pro Lys Ser Leu Leu Ser Leu Glu Leu Lys Asp Asp Arg
            820                 825                 830
```

```
Pro Ala Arg Asp Met Trp Val Met Glu Thr Gly Leu Leu Pro Arg
            835                 840                 845

Ala Thr Ala Gln Asp Ala Gly Lys Tyr Tyr Cys His Arg Gly Asn Leu
    850                 855                 860

Thr Met Ser Phe His Leu Glu Ile Thr Ala Arg Pro Val Leu Trp His
865                 870                 875                 880

Trp Leu Leu Arg Thr Gly Gly Trp Lys Val Ser Ala Val Thr Leu Ala
                885                 890                 895

Tyr Leu Ile Phe Cys Leu Cys Ser Leu Val Gly Ile Leu His Leu Gln
                900                 905                 910

Arg Ala Leu Val Leu Arg Arg Lys Arg
            915                 920

<210> SEQ ID NO 31
<211> LENGTH: 927
<212> TYPE: PRT
<213> ORGANISM: Artificial Sequence
<220> FEATURE:
<223> OTHER INFORMATION: human chimeric Her2scFv-IgG4(HL-CH3)-CD28tm-
      CD28gg-Zeta-T2A-CD19t

<400> SEQUENCE: 31

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Gly Gly Ser Gly Gly Gly Ser Gly Gly Gly
    130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser Glu Ser Lys Tyr Gly
            260                 265                 270
```

```
Pro Pro Cys Pro Pro Cys Pro Gly Gly Gly Ser Ser Gly Gly Gly Ser
        275             280             285
Gly Gly Gln Pro Arg Glu Pro Gln Val Tyr Thr Leu Pro Pro Ser Gln
        290             295             300
Glu Glu Met Thr Lys Asn Gln Val Ser Leu Thr Cys Leu Val Lys Gly
305             310             315             320
Phe Tyr Pro Ser Asp Ile Ala Val Glu Trp Glu Ser Asn Gly Gln Pro
            325             330             335
Glu Asn Asn Tyr Lys Thr Thr Pro Pro Val Leu Asp Ser Asp Gly Ser
        340             345             350
Phe Phe Leu Tyr Ser Arg Leu Thr Val Asp Lys Ser Arg Trp Gln Glu
        355             360             365
Gly Asn Val Phe Ser Cys Ser Val Met His Glu Ala Leu His Asn His
        370             375             380
Tyr Thr Gln Lys Ser Leu Ser Leu Ser Leu Gly Lys Met Phe Trp Val
385             390             395             400
Leu Val Val Val Gly Val Leu Ala Cys Tyr Ser Leu Leu Val Thr
            405             410             415
Val Ala Phe Ile Ile Phe Trp Val Arg Ser Lys Arg Ser Arg Gly Gly
        420             425             430
His Ser Asp Tyr Met Asn Met Thr Pro Arg Arg Pro Gly Pro Thr Arg
        435             440             445
Lys His Tyr Gln Pro Tyr Ala Pro Pro Arg Asp Phe Ala Ala Tyr Arg
        450             455             460
Ser Gly Gly Gly Arg Val Lys Phe Ser Arg Ser Ala Asp Ala Pro Ala
465             470             475             480
Tyr Gln Gln Gly Gln Asn Gln Leu Tyr Asn Glu Leu Asn Leu Gly Arg
            485             490             495
Arg Glu Glu Tyr Asp Val Leu Asp Lys Arg Arg Gly Arg Asp Pro Glu
        500             505             510
Met Gly Gly Lys Pro Arg Arg Lys Asn Pro Gln Glu Gly Leu Tyr Asn
        515             520             525
Glu Leu Gln Lys Asp Lys Met Ala Glu Ala Tyr Ser Glu Ile Gly Met
        530             535             540
Lys Gly Glu Arg Arg Arg Gly Lys Gly His Asp Gly Leu Tyr Gln Gly
545             550             555             560
Leu Ser Thr Ala Thr Lys Asp Thr Tyr Asp Ala Leu His Met Gln Ala
            565             570             575
Leu Pro Pro Arg Leu Glu Gly Gly Gly Glu Gly Arg Gly Ser Leu Leu
        580             585             590
Thr Cys Gly Asp Val Glu Glu Asn Pro Gly Pro Arg Met Pro Pro Pro
        595             600             605
Arg Leu Leu Phe Phe Leu Leu Phe Leu Thr Pro Met Glu Val Arg Pro
        610             615             620
Glu Glu Pro Leu Val Val Lys Val Glu Gly Asp Asn Ala Val Leu
625             630             635             640
Gln Cys Leu Lys Gly Thr Ser Asp Gly Pro Thr Gln Gln Leu Thr Trp
            645             650             655
Ser Arg Glu Ser Pro Leu Lys Pro Phe Leu Lys Leu Ser Leu Gly Leu
        660             665             670
Pro Gly Leu Gly Ile His Met Arg Pro Leu Ala Ile Trp Leu Phe Ile
        675             680             685
```

```
Phe Asn Val Ser Gln Gln Met Gly Gly Phe Tyr Leu Cys Gln Pro Gly
    690                 695                 700
Pro Pro Ser Glu Lys Ala Trp Gln Pro Gly Trp Thr Val Asn Val Glu
705                 710                 715                 720
Gly Ser Gly Glu Leu Phe Arg Trp Asn Val Ser Asp Leu Gly Gly Leu
                725                 730                 735
Gly Cys Gly Leu Lys Asn Arg Ser Ser Glu Gly Pro Ser Ser Pro Ser
                740                 745                 750
Gly Lys Leu Met Ser Pro Lys Leu Tyr Val Trp Ala Lys Asp Arg Pro
                755                 760                 765
Glu Ile Trp Glu Gly Glu Pro Pro Cys Val Pro Arg Asp Ser Leu
    770                 775                 780
Asn Gln Ser Leu Ser Gln Asp Leu Thr Met Ala Pro Gly Ser Thr Leu
785                 790                 795                 800
Trp Leu Ser Cys Gly Val Pro Pro Asp Ser Val Ser Arg Gly Pro Leu
                805                 810                 815
Ser Trp Thr His Val His Pro Lys Gly Pro Lys Ser Leu Leu Ser Leu
                820                 825                 830
Glu Leu Lys Asp Asp Arg Pro Ala Arg Asp Met Trp Val Met Glu Thr
                835                 840                 845
Gly Leu Leu Pro Arg Ala Thr Ala Gln Asp Ala Gly Lys Tyr Tyr
    850                 855                 860
Cys His Arg Gly Asn Leu Thr Met Ser Phe His Leu Glu Ile Thr Ala
865                 870                 875                 880
Arg Pro Val Leu Trp His Trp Leu Leu Arg Thr Gly Gly Trp Lys Val
                885                 890                 895
Ser Ala Val Thr Leu Ala Tyr Leu Ile Phe Cys Leu Cys Ser Leu Val
                900                 905                 910
Gly Ile Leu His Leu Gln Arg Ala Leu Val Leu Arg Arg Lys Arg
    915                 920                 925

<210> SEQ ID NO 32
<211> LENGTH: 808
<212> TYPE: PRT
<213> ORGANISM: Artificial Sequence
<220> FEATURE:
<223> OTHER INFORMATION: human chimeric Her2scFv-Linker-CD28tm-CD28gg-
      Zeta-T2A-CD19t

<400> SEQUENCE: 32

Met Leu Leu Leu Val Thr Ser Leu Leu Leu Cys Glu Leu Pro His Pro
1               5                   10                  15
Ala Phe Leu Leu Ile Pro Asp Ile Gln Met Thr Gln Ser Pro Ser Ser
                20                  25                  30
Leu Ser Ala Ser Val Gly Asp Arg Val Thr Ile Thr Cys Arg Ala Ser
            35                  40                  45
Gln Asp Val Asn Thr Ala Val Ala Trp Tyr Gln Gln Lys Pro Gly Lys
        50                  55                  60
Ala Pro Lys Leu Leu Ile Tyr Ser Ala Ser Phe Leu Tyr Ser Gly Val
65                  70                  75                  80
Pro Ser Arg Phe Ser Gly Ser Arg Ser Gly Thr Asp Phe Thr Leu Thr
                85                  90                  95
Ile Ser Ser Leu Gln Pro Glu Asp Phe Ala Thr Tyr Tyr Cys Gln Gln
                100                 105                 110
His Tyr Thr Thr Pro Pro Thr Phe Gly Gln Gly Thr Lys Val Glu Ile
            115                 120                 125
```

```
Lys Gly Ser Thr Ser Gly Gly Ser Gly Gly Ser Gly Gly Gly
    130                 135                 140
Gly Ser Ser Glu Val Gln Leu Val Glu Ser Gly Gly Leu Val Gln
145                 150                 155                 160
Pro Gly Gly Ser Leu Arg Leu Ser Cys Ala Ala Ser Gly Phe Asn Ile
                165                 170                 175
Lys Asp Thr Tyr Ile His Trp Val Arg Gln Ala Pro Gly Lys Gly Leu
            180                 185                 190
Glu Trp Val Ala Arg Ile Tyr Pro Thr Asn Gly Tyr Thr Arg Tyr Ala
        195                 200                 205
Asp Ser Val Lys Gly Arg Phe Thr Ile Ser Ala Asp Thr Ser Lys Asn
    210                 215                 220
Thr Ala Tyr Leu Gln Met Asn Ser Leu Arg Ala Glu Asp Thr Ala Val
225                 230                 235                 240
Tyr Tyr Cys Ser Arg Trp Gly Asp Gly Phe Tyr Ala Met Asp Tyr
                245                 250                 255
Trp Gly Gln Gly Thr Leu Val Thr Val Ser Ser Gly Gly Ser Ser
            260                 265                 270
Gly Gly Gly Ser Gly Met Phe Trp Val Leu Val Val Gly Gly Val
        275                 280                 285
Leu Ala Cys Tyr Ser Leu Leu Val Thr Val Ala Phe Ile Ile Phe Trp
290                 295                 300
Val Arg Ser Lys Arg Ser Arg Gly Gly His Ser Asp Tyr Met Asn Met
305                 310                 315                 320
Thr Pro Arg Arg Pro Gly Pro Thr Arg Lys His Tyr Gln Pro Tyr Ala
                325                 330                 335
Pro Pro Arg Asp Phe Ala Ala Tyr Arg Ser Gly Gly Gly Arg Val Lys
            340                 345                 350
Phe Ser Arg Ser Ala Asp Ala Pro Ala Tyr Gln Gln Gly Gln Asn Gln
        355                 360                 365
Leu Tyr Asn Glu Leu Asn Leu Gly Arg Arg Glu Glu Tyr Asp Val Leu
    370                 375                 380
Asp Lys Arg Arg Gly Arg Asp Pro Glu Met Gly Gly Lys Pro Arg Arg
385                 390                 395                 400
Lys Asn Pro Gln Glu Gly Leu Tyr Asn Glu Leu Gln Lys Asp Lys Met
                405                 410                 415
Ala Glu Ala Tyr Ser Glu Ile Gly Met Lys Gly Glu Arg Arg Arg Gly
            420                 425                 430
Lys Gly His Asp Gly Leu Tyr Gln Gly Leu Ser Thr Ala Thr Lys Asp
        435                 440                 445
Thr Tyr Asp Ala Leu His Met Gln Ala Leu Pro Pro Arg Leu Glu Gly
    450                 455                 460
Gly Gly Glu Gly Arg Gly Ser Leu Leu Thr Cys Gly Asp Val Glu Glu
465                 470                 475                 480
Asn Pro Gly Pro Arg Met Pro Pro Arg Leu Leu Phe Phe Leu Leu
                485                 490                 495
Phe Leu Thr Pro Met Glu Val Arg Pro Glu Glu Pro Leu Val Val Lys
            500                 505                 510
Val Glu Glu Gly Asp Asn Ala Val Leu Gln Cys Leu Lys Gly Thr Ser
        515                 520                 525
Asp Gly Pro Thr Gln Gln Leu Thr Trp Ser Arg Glu Ser Pro Leu Lys
    530                 535                 540
```

```
Pro Phe Leu Lys Leu Ser Leu Gly Leu Pro Leu Gly Ile His Met
545                 550                 555                 560

Arg Pro Leu Ala Ile Trp Leu Phe Ile Phe Asn Val Ser Gln Gln Met
                565                 570                 575

Gly Gly Phe Tyr Leu Cys Gln Pro Gly Pro Ser Glu Lys Ala Trp
            580                 585                 590

Gln Pro Gly Trp Thr Val Asn Val Glu Gly Ser Gly Glu Leu Phe Arg
        595                 600                 605

Trp Asn Val Ser Asp Leu Gly Leu Gly Cys Gly Leu Lys Asn Arg
    610                 615                 620

Ser Ser Glu Gly Pro Ser Pro Ser Gly Lys Leu Met Ser Pro Lys
625                 630                 635                 640

Leu Tyr Val Trp Ala Lys Asp Arg Pro Glu Ile Trp Glu Gly Glu Pro
                645                 650                 655

Pro Cys Val Pro Pro Arg Asp Ser Leu Asn Gln Ser Leu Ser Gln Asp
                660                 665                 670

Leu Thr Met Ala Pro Gly Ser Thr Leu Trp Leu Ser Cys Gly Val Pro
            675                 680                 685

Pro Asp Ser Val Ser Arg Gly Pro Leu Ser Trp Thr His Val His Pro
690                 695                 700

Lys Gly Pro Lys Ser Leu Leu Ser Leu Glu Leu Lys Asp Asp Arg Pro
705                 710                 715                 720

Ala Arg Asp Met Trp Val Met Glu Thr Gly Leu Leu Leu Pro Arg Ala
                725                 730                 735

Thr Ala Gln Asp Ala Gly Lys Tyr Tyr Cys His Arg Gly Asn Leu Thr
            740                 745                 750

Met Ser Phe His Leu Glu Ile Thr Ala Arg Pro Val Leu Trp His Trp
        755                 760                 765

Leu Leu Arg Thr Gly Gly Trp Lys Val Ser Ala Val Thr Leu Ala Tyr
    770                 775                 780

Leu Ile Phe Cys Leu Cys Ser Leu Val Gly Ile Leu His Leu Gln Arg
785                 790                 795                 800

Ala Leu Val Leu Arg Arg Lys Arg
                805
```

<210> SEQ ID NO 33
<211> LENGTH: 802
<212> TYPE: PRT
<213> ORGANISM: Artificial Sequence
<220> FEATURE:
<223> OTHER INFORMATION: human chimeric Her2scFv-Linker-CD8tm-41BB-Zeta-T2A-CD19t

<400> SEQUENCE: 33

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95
```

```
Ile Ser Ser Leu Gln Pro Glu Asp Phe Ala Thr Tyr Tyr Cys Gln Gln
                100                 105                 110

His Tyr Thr Thr Pro Pro Thr Phe Gly Gln Gly Thr Lys Val Glu Ile
            115                 120                 125

Lys Gly Ser Thr Ser Gly Gly Gly Ser Gly Gly Gly Ser Gly Gly Gly
        130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Asp Gly Phe Tyr Ala Met Asp Tyr
                245                 250                 255

Trp Gly Gln Gly Thr Leu Val Thr Val Ser Ser Gly Gly Gly Ser Ser
        260                 265                 270

Gly Gly Gly Ser Gly Ile Tyr Ile Trp Ala Pro Leu Ala Gly Thr Cys
        275                 280                 285

Gly Val Leu Leu Leu Ser Leu Val Ile Thr Lys Arg Gly Arg Lys Lys
    290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
            325                 330                 335

Gly Cys Glu Leu Gly Gly Gly Arg Val Lys Phe Ser Arg Ser Ala Asp
        340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg Leu Glu Gly Gly Gly Glu Gly Arg Gly
    450                 455                 460

Ser Leu Leu Thr Cys Gly Asp Val Glu Glu Asn Pro Gly Pro Arg Met
465                 470                 475                 480

Pro Pro Pro Arg Leu Leu Phe Phe Leu Leu Phe Leu Thr Pro Met Glu
                485                 490                 495

Val Arg Pro Glu Glu Pro Leu Val Val Lys Val Glu Glu Gly Asp Asn
            500                 505                 510
```

```
Ala Val Leu Gln Cys Leu Lys Gly Thr Ser Asp Gly Pro Thr Gln Gln
            515                 520                 525

Leu Thr Trp Ser Arg Glu Ser Pro Leu Lys Pro Phe Leu Lys Leu Ser
        530                 535                 540

Leu Gly Leu Pro Gly Leu Gly Ile His Met Arg Pro Leu Ala Ile Trp
545                 550                 555                 560

Leu Phe Ile Phe Asn Val Ser Gln Gln Met Gly Gly Phe Tyr Leu Cys
                565                 570                 575

Gln Pro Gly Pro Pro Ser Glu Lys Ala Trp Gln Pro Gly Trp Thr Val
            580                 585                 590

Asn Val Glu Gly Ser Gly Glu Leu Phe Arg Trp Asn Val Ser Asp Leu
        595                 600                 605

Gly Gly Leu Gly Cys Gly Leu Lys Asn Arg Ser Ser Glu Gly Pro Ser
610                 615                 620

Ser Pro Ser Gly Lys Leu Met Ser Pro Lys Leu Tyr Val Trp Ala Lys
625                 630                 635                 640

Asp Arg Pro Glu Ile Trp Glu Gly Glu Pro Pro Cys Val Pro Pro Arg
            645                 650                 655

Asp Ser Leu Asn Gln Ser Leu Ser Gln Asp Leu Thr Met Ala Pro Gly
            660                 665                 670

Ser Thr Leu Trp Leu Ser Cys Gly Val Pro Pro Asp Ser Val Ser Arg
            675                 680                 685

Gly Pro Leu Ser Trp Thr His Val His Pro Lys Gly Pro Lys Ser Leu
            690                 695                 700

Leu Ser Leu Glu Leu Lys Asp Asp Arg Pro Ala Arg Asp Met Trp Val
705                 710                 715                 720

Met Glu Thr Gly Leu Leu Leu Pro Arg Ala Thr Ala Gln Asp Ala Gly
                725                 730                 735

Lys Tyr Tyr Cys His Arg Gly Asn Leu Thr Met Ser Phe His Leu Glu
                740                 745                 750

Ile Thr Ala Arg Pro Val Leu Trp His Trp Leu Leu Arg Thr Gly Gly
            755                 760                 765

Trp Lys Val Ser Ala Val Thr Leu Ala Tyr Leu Ile Phe Cys Leu Cys
770                 775                 780

Ser Leu Val Gly Ile Leu His Leu Gln Arg Ala Leu Val Leu Arg Arg
785                 790                 795                 800

Lys Arg

<210> SEQ ID NO 34
<211> LENGTH: 658
<212> TYPE: PRT
<213> ORGANISM: Artificial Sequence
<220> FEATURE:
<223> OTHER INFORMATION: human chimeric Her2scFv-IgG4(L235E,
      N297Q)-CD28tm-CD28gg-Zeta-T2A-CD19t minus leader, TSA or CD19t

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
            115                 120                 125

Leu Val Glu Ser Gly Gly Gly Leu Val Gln Pro Gly Gly Ser Leu Arg
        130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
210                 215                 220

Gly Gly Asp Gly Phe Tyr Ala Met Asp Tyr Trp Gly Gln Gly Thr Leu
225                 230                 235                 240

Val Thr Val Ser Ser Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
290                 295                 300

Tyr Val Asp Gly Val Glu Val His Asn Ala Lys Thr Lys Pro Arg Glu
305                 310                 315                 320

Glu Gln Phe Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
            450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
```

```
                    485                 490                 495
Phe Ile Ile Phe Trp Val Arg Ser Lys Arg Ser Arg Gly Gly His Ser
                500                 505                 510

Asp Tyr Met Asn Met Thr Pro Arg Arg Pro Gly Pro Thr Arg Lys His
            515                 520                 525

Tyr Gln Pro Tyr Ala Pro Pro Arg Asp Phe Ala Ala Tyr Arg Ser Gly
        530                 535                 540

Gly Gly Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
        610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg
```

<210> SEQ ID NO 35
<211> LENGTH: 652
<212> TYPE: PRT
<213> ORGANISM: Artificial Sequence
<220> FEATURE:
<223> OTHER INFORMATION: human chimeric
    Her2scFv-IgG4(L235E,N297Q)-CD8tm-41BB-Zeta-T2A-CD19t  minus
    leader, TSA or CD19t

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175
```

-continued

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Ile Tyr Ile Trp Ala Pro
465                 470                 475                 480

Leu Ala Gly Thr Cys Gly Val Leu Leu Leu Ser Leu Val Ile Thr Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Gly Gly Gly Arg Val Lys Phe
    530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
            580                 585                 590

Asn Pro Gln Glu Gly Leu Tyr Asn Glu Leu Gln Lys Asp Lys Met Ala

```
                595                 600                 605
Glu Ala Tyr Ser Glu Ile Gly Met Lys Gly Glu Arg Arg Gly Lys
            610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650

<210> SEQ ID NO 36
<211> LENGTH: 474
<212> TYPE: PRT
<213> ORGANISM: Artificial Sequence
<220> FEATURE:
<223> OTHER INFORMATION: human chimeric Her2scFv-CD8hinge-CD8tm-41BB-
      Zeta-T2A-CD19t minus leader, TSA or CD19t

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Gly Ser Thr Ser Gly
        100                 105                 110

Gly Gly Ser Gly Gly Gly Ser Gly Gly Gly Ser Ser Glu Val Gln
    115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Ala Lys Pro Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300
```

```
Gly Val Leu Leu Leu Ser Leu Val Ile Thr Gly Gly Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Gly Gly Arg Val Lys Phe Ser Arg
                355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
                420                 425                 430

Tyr Ser Glu Ile Gly Met Lys Gly Glu Arg Arg Arg Gly Lys Gly His
                435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 37
<211> LENGTH: 445
<212> TYPE: PRT
<213> ORGANISM: Artificial Sequence
<220> FEATURE:
<223> OTHER INFORMATION: human chimeric Her2scFv-Hinge-Linker-CD8tm-
      41BB-Zeta-T2A-CD19t minus leader, TSA or CD19t

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
                100                 105                 110

Gly Gly Ser Gly Gly Gly Ser Gly Gly Gly Ser Ser Glu Val Gln
            115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
                180                 185                 190
```

```
Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ser Arg Trp
        210                 215                 220

Gly Gly Asp Gly Phe Tyr Ala Met Asp Tyr Trp Gly Gln Gly Thr Leu
225                 230                 235                 240

Val Thr Val Ser Ser Glu Ser Lys Tyr Gly Pro Pro Cys Pro Pro Cys
            245                 250                 255

Pro Gly Gly Gly Ser Gly Gly Gly Ser Gly Ile Tyr Ile Trp Ala
        260                 265                 270

Pro Leu Ala Gly Thr Cys Gly Val Leu Leu Leu Ser Leu Val Ile Thr
            275                 280                 285

Lys Arg Gly Arg Lys Lys Leu Leu Tyr Ile Phe Lys Gln Pro Phe Met
        290                 295                 300

Arg Pro Val Gln Thr Thr Gln Glu Glu Asp Gly Cys Ser Cys Arg Phe
305                 310                 315                 320

Pro Glu Glu Glu Glu Gly Gly Cys Glu Leu Gly Gly Arg Val Lys
            325                 330                 335

Phe Ser Arg Ser Ala Asp Ala Pro Ala Tyr Gln Gln Gly Gln Asn Gln
        340                 345                 350

Leu Tyr Asn Glu Leu Asn Leu Gly Arg Arg Glu Glu Tyr Asp Val Leu
            355                 360                 365

Asp Lys Arg Arg Gly Arg Asp Pro Glu Met Gly Gly Lys Pro Arg Arg
370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
            405                 410                 415

Lys Gly His Asp Gly Leu Tyr Gln Gly Leu Ser Thr Ala Thr Lys Asp
        420                 425                 430

Thr Tyr Asp Ala Leu His Met Gln Ala Leu Pro Pro Arg
            435                 440                 445

<210> SEQ ID NO 38
<211> LENGTH: 552
<212> TYPE: PRT
<213> ORGANISM: Artificial Sequence
<220> FEATURE:
<223> OTHER INFORMATION: human chimeric Her2scFv-IgG4(HL-CH3)-CD8tm-
      41BB-Zeta-T2A-CD19t minus leader, TSA or CD19t

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
```

```
            100                 105                 110
Gly Gly Ser Gly Gly Ser Gly Gly Gly Ser Ser Glu Val Gln
            115                 120                 125
Leu Val Glu Ser Gly Gly Leu Val Gln Pro Gly Gly Ser Leu Arg
            130                 135             140
Leu Ser Cys Ala Ala Ser Gly Phe Asn Ile Lys Asp Thr Tyr Ile His
145                 150                 155                 160
Trp Val Arg Gln Ala Pro Gly Lys Gly Leu Glu Trp Val Ala Arg Ile
                165                 170                 175
Tyr Pro Thr Asn Gly Tyr Thr Arg Tyr Ala Asp Ser Val Lys Gly Arg
                180                 185                 190
Phe Thr Ile Ser Ala Asp Thr Ser Lys Asn Thr Ala Tyr Leu Gln Met
        195                 200                 205
Asn Ser Leu Arg Ala Glu Asp Thr Ala Val Tyr Tyr Cys Ser Arg Trp
        210                 215                 220
Gly Gly Asp Gly Phe Tyr Ala Met Asp Tyr Trp Gly Gln Gly Thr Leu
225                 230                 235                 240
Val Thr Val Ser Ser Glu Ser Lys Tyr Gly Pro Pro Cys Pro Pro Cys
                245                 250                 255
Pro Gly Gly Gly Ser Ser Gly Gly Gly Ser Gly Gly Gln Pro Arg Glu
                260                 265                 270
Pro Gln Val Tyr Thr Leu Pro Pro Ser Gln Glu Glu Met Thr Lys Asn
            275                 280                 285
Gln Val Ser Leu Thr Cys Leu Val Lys Gly Phe Tyr Pro Ser Asp Ile
        290                 295                 300
Ala Val Glu Trp Glu Ser Asn Gly Gln Pro Glu Asn Asn Tyr Lys Thr
305                 310                 315                 320
Thr Pro Pro Val Leu Asp Ser Asp Gly Ser Phe Phe Leu Tyr Ser Arg
                325                 330                 335
Leu Thr Val Asp Lys Ser Arg Trp Gln Glu Gly Asn Val Phe Ser Cys
                340                 345                 350
Ser Val Met His Glu Ala Leu His Asn His Tyr Thr Gln Lys Ser Leu
            355                 360                 365
Ser Leu Ser Leu Gly Lys Ile Tyr Ile Trp Ala Pro Leu Ala Gly Thr
        370                 375                 380
Cys Gly Val Leu Leu Leu Ser Leu Val Ile Thr Lys Arg Gly Arg Lys
385                 390                 395                 400
Lys Leu Leu Tyr Ile Phe Lys Gln Pro Phe Met Arg Pro Val Gln Thr
                405                 410                 415
Thr Gln Glu Glu Asp Gly Cys Ser Cys Arg Phe Pro Glu Glu Glu Glu
            420                 425                 430
Gly Gly Cys Glu Leu Gly Gly Gly Arg Val Lys Phe Ser Arg Ser Ala
            435                 440                 445
Asp Ala Pro Ala Tyr Gln Gln Gly Gln Asn Gln Leu Tyr Asn Glu Leu
        450                 455                 460
Asn Leu Gly Arg Arg Glu Glu Tyr Asp Val Leu Asp Lys Arg Arg Gly
465                 470                 475                 480
Arg Asp Pro Glu Met Gly Gly Lys Pro Arg Arg Lys Asn Pro Gln Glu
                485                 490                 495
Gly Leu Tyr Asn Glu Leu Gln Lys Asp Lys Met Ala Glu Ala Tyr Ser
            500                 505                 510
Glu Ile Gly Met Lys Gly Glu Arg Arg Arg Gly Lys Gly His Asp Gly
            515                 520                 525
```

Leu Tyr Gln Gly Leu Ser Thr Ala Thr Lys Asp Thr Tyr Asp Ala Leu
             530                 535                 540

His Met Gln Ala Leu Pro Pro Arg
545                 550

<210> SEQ ID NO 39
<211> LENGTH: 558
<212> TYPE: PRT
<213> ORGANISM: Artificial Sequence
<220> FEATURE:
<223> OTHER INFORMATION: human chimeric Her2scFv-IgG4(HL-CH3)-CD28tm-
      CD28gg-Zeta-T2A-CD19t minus leader, TSA or CD19t

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Glu Ser Lys Tyr Gly Pro Pro Cys Pro Pro Cys
                245                 250                 255

Pro Gly Gly Gly Ser Ser Gly Gly Gly Ser Gly Gly Gln Pro Arg Glu
            260                 265                 270

Pro Gln Val Tyr Thr Leu Pro Pro Ser Gln Glu Glu Met Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Arg

```
                325                 330                 335
Leu Thr Val Asp Lys Ser Arg Trp Gln Glu Gly Asn Val Phe Ser Cys
            340                 345                 350
Ser Val Met His Glu Ala Leu His Asn His Tyr Thr Gln Lys Ser Leu
        355                 360                 365
Ser Leu Ser Leu Gly Lys Met Phe Trp Val Leu Val Val Val Gly Gly
    370                 375                 380
Val Leu Ala Cys Tyr Ser Leu Leu Val Thr Val Ala Phe Ile Ile Phe
385                 390                 395                 400
Trp Val Arg Ser Lys Arg Ser Arg Gly Gly His Ser Asp Tyr Met Asn
                405                 410                 415
Met Thr Pro Arg Arg Pro Gly Pro Thr Arg Lys His Tyr Gln Pro Tyr
            420                 425                 430
Ala Pro Pro Arg Asp Phe Ala Ala Tyr Arg Ser Gly Gly Gly Arg Val
        435                 440                 445
Lys Phe Ser Arg Ser Ala Asp Ala Pro Ala Tyr Gln Gln Gly Gln Asn
    450                 455                 460
Gln Leu Tyr Asn Glu Leu Asn Leu Gly Arg Arg Glu Glu Tyr Asp Val
465                 470                 475                 480
Leu Asp Lys Arg Arg Gly Arg Asp Pro Glu Met Gly Gly Lys Pro Arg
                485                 490                 495
Arg Lys Asn Pro Gln Glu Gly Leu Tyr Asn Glu Leu Gln Lys Asp Lys
            500                 505                 510
Met Ala Glu Ala Tyr Ser Glu Ile Gly Met Lys Gly Glu Arg Arg Arg
        515                 520                 525
Gly Lys Gly His Asp Gly Leu Tyr Gln Gly Leu Ser Thr Ala Thr Lys
    530                 535                 540
Asp Thr Tyr Asp Ala Leu His Met Gln Ala Leu Pro Pro Arg
545                 550                 555

<210> SEQ ID NO 40
<211> LENGTH: 439
<212> TYPE: PRT
<213> ORGANISM: Artificial Sequence
<220> FEATURE:
<223> OTHER INFORMATION: human chimeric Her2scFv-Linker-CD28tm-CD28gg-
      Zeta-T2A-CD19t minus leader, TSA or CD19t

<400> SEQUENCE: 40

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Gly Ser Thr Ser Gly
            100                 105                 110
Gly Gly Ser Gly Gly Gly Ser Gly Gly Gly Ser Ser Glu Val Gln
        115                 120                 125
```

```
Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Gly Gly Ser Gly Gly Ser Gly Met
                245                 250                 255

Phe Trp Val Leu Val Val Val Gly Gly Val Leu Ala Cys Tyr Ser Leu
                260                 265                 270

Leu Val Thr Val Ala Phe Ile Ile Phe Trp Val Arg Ser Lys Arg Ser
        275                 280                 285

Arg Gly Gly His Ser Asp Tyr Met Asn Met Thr Pro Arg Arg Pro Gly
    290                 295                 300

Pro Thr Arg Lys His Tyr Gln Pro Tyr Ala Pro Pro Arg Asp Phe Ala
305                 310                 315                 320

Ala Tyr Arg Ser Gly Gly Gly Arg Val Lys Phe Ser Arg Ser Ala Asp
                325                 330                 335

Ala Pro Ala Tyr Gln Gln Gly Gln Asn Gln Leu Tyr Asn Glu Leu Asn
            340                 345                 350

Leu Gly Arg Arg Glu Glu Tyr Asp Val Leu Asp Lys Arg Arg Gly Arg
        355                 360                 365

Asp Pro Glu Met Gly Gly Lys Pro Arg Arg Lys Asn Pro Gln Glu Gly
    370                 375                 380

Leu Tyr Asn Glu Leu Gln Lys Asp Lys Met Ala Glu Ala Tyr Ser Glu
385                 390                 395                 400

Ile Gly Met Lys Gly Glu Arg Arg Arg Gly Lys Gly His Asp Gly Leu
                405                 410                 415

Tyr Gln Gly Leu Ser Thr Ala Thr Lys Asp Thr Tyr Asp Ala Leu His
            420                 425                 430

Met Gln Ala Leu Pro Pro Arg
        435

<210> SEQ ID NO 41
<211> LENGTH: 433
<212> TYPE: PRT
<213> ORGANISM: Artificial Sequence
<220> FEATURE:
<223> OTHER INFORMATION: human chimeric Her2scFv-Linker-CD8tm-41BB-Zeta-
      T2A-CD19t minus leader, TSA or CD19t

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Gly Ser Thr Ser Gly
                100                 105                 110

Gly Gly Ser Gly Gly Gly Ser Gly Gly Gly Ser Ser Glu Val Gln
                115                 120                 125

Leu Val Glu Ser Gly Gly Gly Leu Val Gln Pro Gly Gly Ser Leu Arg
        130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
                180                 185                 190

Phe Thr Ile Ser Ala Asp Thr Ser Lys Asn Thr Ala Tyr Leu Gln Met
                195                 200                 205

Asn Ser Leu Arg Ala Glu Asp Thr Ala Val Tyr Tyr Cys Ser Arg Trp
210                 215                 220

Gly Gly Asp Gly Phe Tyr Ala Met Asp Tyr Trp Gly Gln Gly Thr Leu
225                 230                 235                 240

Val Thr Val Ser Ser Gly Gly Gly Ser Ser Gly Gly Gly Ser Gly Ile
                245                 250                 255

Tyr Ile Trp Ala Pro Leu Ala Gly Thr Cys Gly Val Leu Leu Leu Ser
                260                 265                 270

Leu Val Ile Thr Lys Arg Gly Arg Lys Lys Leu Leu Tyr Ile Phe Lys
                275                 280                 285

Gln Pro Phe Met Arg Pro Val Gln Thr Thr Gln Glu Glu Asp Gly Cys
        290                 295                 300

Ser Cys Arg Phe Pro Glu Glu Glu Glu Gly Gly Cys Glu Leu Gly Gly
305                 310                 315                 320

Gly Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
                340                 345                 350

Tyr Asp Val Leu Asp Lys Arg Gly Arg Asp Pro Glu Met Gly Gly
        355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
                420                 425                 430

Arg

<210> SEQ ID NO 42
<211> LENGTH: 22
<212> TYPE: PRT

```
<213> ORGANISM: Artificial Sequence
<220> FEATURE:
<223> OTHER INFORMATION: hinge-linker domain

<400> SEQUENCE: 42

Glu Ser Lys Tyr Gly Pro Pro Cys Pro Pro Cys Pro Gly Gly Ser
1               5                   10                  15

Ser Gly Gly Gly Ser Gly
            20
```

CHIMERIC ANTIGEN RECEPTORS TARGETING HER2

CROSS-REFERENCE TO RELATED APPLICATION

This application is a National Stage Application under 35 U.S.C. § 371 and claims the benefit of International Application No. PCT/US2016/060724, filed Nov. 4, 2016, which claims priority to U.S. Application No. 62/251,052, filed Nov. 4, 2015. The disclosure of the foregoing application is hereby incorporated by reference in its entirety.

BACKGROUND

Tumor-specific T cell based immunotherapies, including therapies employing engineered T cells, have been investigated for anti-tumor treatment. In some cases the T cells used in such therapies do not remain active in vivo for long enough periods. In some cases, the tumor-specificity of the T cells is relatively low, in part because of the heterogeneous nature of solid tumors and the potential for off-target effects on non-cancerous cells when targeting self antigens. Therefore, there is a need in the art for tumor-specific cancer therapies with improved anti-tumor specificity and function.

Chimeric antigen receptors (CARs) are composed of an extracellular tumor recognition/targeting domain, an extracellular linker/spacer, a transmembrane domain, and intracellular T cell-activating and co-stimulatory signaling domains. The design of the recognition/targeting domain is critical to avoiding deleterious off-target effects. The majority of CAR tumor targeting domains are single chain variable fragments (scFvs) derived from antibody sequences that exploit the specificity of antibody binding to particular antigens. There are also examples of CAR tumor targeting domains derived from normal receptor ligands, such as the IL-13 cytokine CAR that targets cells expressing the IL-13 receptor, IL13Rα2.

Adoptive T cell therapy (ACT) utilizing engineered T cells expressing a CAR has demonstrated robust and durable clinical efficacy in patients with CD 19+ B-cell malignancies (Priceman et al. 2015 *Curr Opin Oncol*; Maus et al. 2014 *Blood* 123: 2625-2635. With early successes in hematologic diseases, broader application of this approach to solid tumors is now under intense investigation.

According to the National Cancer Institute Surveillance, Epidemiology, and End Results Program (SEER) data, there were an estimated 40,000 deaths from breast cancer in 2014, primarily from metastatic disease. Approximately 25-30% of breast cancer patients carry an amplification of the HER2 gene, which confers a particularly poor prognosis. Even with the advent of newer agents, including targeted therapies, there have been only modest improvements in overall mortality rates in Stage IV disease. For example, in a randomized trial with HER2-positive breast cancer patients, the most promising treatment combination of two HER2-targeted antibodies, trastuzumab and pertuzumab, plus docetaxel yields a median overall survival of 56.5 months and an extension of progression-free survival of only 6.3 months over trastuzumab and docetaxel alone.

SUMMARY

Described herein are chimeric transmembrane immunoreceptors (chimeric antigen receptors or "CARs") which comprise an extracellular domain, a transmembrane region and an intracellular signaling domain. The extracellular domain includes a scFv targeted to HER2 and, optionally, a spacer, comprising, for example, a portion of human Fe domain. The transmembrane portion includes, for example, a CD4 transmembrane domain, a CD8 transmembrane domain, a CD28 transmembrane domain, or a CD3 transmembrane domain. The intracellular signaling domain includes the signaling domain from the zeta chain of the human CD3 complex (CD3ξ) and one or more costimulatory domains, for example, a 4-IBB or a CD28 costimulatory domain. The extracellular domain enables the CAR, when expressed on the surface of a T cell, to direct T cell activity to those cells expressing HER2. Such cells include certain breast cancer cells and certain brain cancer cells. The inclusion of a costimulatory domain, such as the 4-IBB (CD137) costimulatory domain in series with CD3ξ in the intracellular region enables the T cell to receive co-stimulatory signals. T cells, for example, patient-specific, autologous T cells can be engineered to express the CARs described herein, and the engineered cells can be expanded and used in ACT. Various T cell subsets, including both alpha beta T cells and gamma delta T cells, can be used. In addition, the CAR can be expressed in other immune cells such as NK cells. Where a patient is treated with an immune cell expressing a CAR described herein the cell can be an autologous T cell or an allogenic T cell. In some cases the cells used are a cell population that includes both CD4+ and CD8+ central memory T cells ($T_{CM}$), which are CD62L+, CCR7+, CD45RO+, and CD45RA−, or the cells used are a cell population that includes CD4+ and CD8+$T_{CM}$ cells, stem central memory T cells and naive T cells (i.e., a population of $T_{CM/SCM/N}$ cells). A population of $T_{CM/SCM/N}$ cells are CD62L+, CCR7+ and include both CD45RA+ and CD45RO+ cells as well as both CD4+ cells and CD8+ cells. The use of such cells can improve long-term persistence of the cells after adoptive transfer compared to the use of other types of patient-specific T cells.

Described herein is a nucleic acid molecule encoding a CAR comprising: an scFv targeted to HER2 (e.g., DIQMTQSPSSLSASVGDRVTITCRASQDVNTA-VAWYQQKPGKAPKLLIYSASFLY SGVPSRFSGSRSGTDFTLTISSLQPEDFA-TYYCQQHYTTPPTFGQGTKVEIKGSTSG GGSGGGSGGGGSSEVQLVESGGGLVQPGGSLRLS-CAASGFNIKDTYIHWVRQAP GKGLEW-VARIYPTNGYTRYADSVKGRFTISADTSKNTAY-LQMNSLRAEDTAVY YCSRWGGDGFYAMDYWGQGTLVTVSS; SEQ ID NO: 1) or a variant thereof having 1-5 (e.g., 1 or 2) amino acid modifications (e.g., substitutions); a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ξ transmembrane domain or a variant thereof having 1-5 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and a CD3ξ signaling domain or a variant thereof having 1-5 (e.g., 1 or 2) amino acid modifications:

In various embodiments: the costimulatory domain is selected from the group consisting of: a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions.

In some cases there is a short sequence of 1-6 amino acids (e.g. GGG) between the co-stimulatory domains and the CD3ξ signaling domain and/or between the two co-stimulatory domains.

Additional embodiment the CAR comprises: an scFv targeted to HER2; two different costimulatory domains selected from the group consisting of: a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications; two different costimulatory domains selected from the group consisting of: a CD28 costimulatory domain or a variant thereof having 1-2 amino acid modifications, a 4-1BB costimulatory domain or a variant thereof having 1-2 amino acid modifications and an OX40 costimulatory domain or a variant thereof having 1-2 amino acid modifications; a HER2 scFv or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3 transmembrane domain or a variant thereof having 1-2 amino acid modifications; a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ξ signaling domain of a variant thereof having 1-2 amino acid modifications; a spacer region located between the HER2 scFv or variant thereof and the transmembrane domain (e.g., the spacer region comprises an amino acid sequence selected from the group consisting of SEQ ID NOs: 2-12 and 42 (Table 3) or a variant thereof having 1-5 (e.g., 1 or 2) amino acid modifications); the spacer comprises an IgG hinge region; the spacer region comprises 1-150 amino acids; there is no spacer; the 4-1 BB signaling domain comprises the amino acid sequence of SEQ ID NO:24 the CD3 signaling domain comprises the amino acid sequence of SEQ ID NO:21 and a linker of 3 to 15 amino acids that is located between the costimulatory domain and the CD3 signaling domain or variant thereof. In certain embodiments where there are two costimulatory domains, one is a 4-1BB costimulatory domain and the other a costimulatory domain selected from: CD28 and CD28gg. In various embodiments the 1-5 (e.g., 1 or 2) amino acid modification are substitutions, e.g., conservative substitutions.

In some embodiments: nucleic acid molecule expresses a polypeptide comprising an amino acid sequence selected from SEQ ID NOs: 26-41; the chimeric antigen receptor comprises an amino acid sequence selected from SEQ ID NOs: 26-41.

Also disclosed is a population of human T cells transduced by a vector comprising an expression cassette encoding a chimeric antigen receptor, wherein chimeric antigen receptor comprises: an scFv targeted to HER2; a transmembrane domain selected from: a CD4 transmembrane domain or variant thereof having 1-5 amino acid modifications (e.g., 1 or 2) amino acid modifications (e.g., substitutions), a CD8 transmembrane domain or variant thereof having 1-5 amino acid modifications (e.g., 1 or 2) amino acid modifications (e.g., substitutions), a CD28 transmembrane domain or a variant thereof having 1-5 amino acid modifications (e.g., 1 or 2) amino acid modifications (e.g., substitutions), and a CD3ξ transmembrane domain or a variant thereof having 1-5 amino acid modifications (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1 BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3ξ signaling domain of a variant thereof having 1-5 amino acid modifications (e.g., 1 or 2) amino acid modifications (e.g., substitutions). In various embodiments: the population of human T cells comprise a vector expressing a chimeric antigen receptor comprising an amino acid sequence selected from any of SEQ ID NOs: 26-41 or a variant thereof having 1-5 amino acid modifications (e.g., 1 or 2) amino acid modifications (e.g., substitutions); the population of human T cells comprises central memory T cells ($T_{CM}$ cells) e.g., at least 20%, 30%, 40%, 50% 60%, 70%, 80% of the cells are $T_{CM}$ cells, or the population of T cells comprises a combination of central memory T cells, naive T cells and stem central memory cells ($T_{CM/SCM/N}$ cells) e.g., at least 20%, 30%, 40%, 50% 60%, 70%, 80% of the cells are $T_{CM/SCM/N}$ cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells).

Also described is a method of treating cancer in a patient comprising administering a population of autologous or allogeneic human T cells (e.g., autologous or allogenic T cells comprising central memory T cells ($T_{CM}$ cells) or a combination of central memory T cells, naive T cells and stem central memory cells (i.e., the T cells are $T_{CM/SCM/N}$ cells) at least 20%, 30%, 40%, 50% 60%, 70%, 80% of the cells are $T_{CM/SCM/N}$ cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells) transduced by a vector comprising an expression cassette encoding a chimeric antigen receptor, wherein chimeric antigen receptor comprises an amino acid sequence selected from SEQ ID NOs: 26-41 or a variant thereof having 1-5 (e.g., 1 or 2) amino acid modifications (e.g., substitutions). In various embodiments: the cancer is brain cancer, e.g., an HER2-expressing brain cancer that is a metastasis from breast cancer; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 26 or 27 or a variant thereof having 1-5 (e.g., 1 or 2) amino acid modifications (e.g., substitutions). In some cases the CAR T cells are administered not directly the brain tumor, but are instead administered to the intraventricular space within the brain of the patient.

Also described is: a nucleic acid molecule encoding a polypeptide comprising an amino acid sequence that is at least 95% identical to an amino acid sequence selected from SEQ ID NOs 26-41; a nucleic acid molecule encoding an polypeptide comprising an amino acid sequence that is identical to an amino acid sequence selected from SEQ ID NOs: 26-41 except for the presence of no more than 5 amino acid substitutions, deletions or insertions; a nucleic acid molecule encoding an polypeptide comprising an amino acid sequence that is identical to an amino acid sequence selected from SEQ ID NOs:26-41 except for the presence of no more than 5 amino acid substitutions; and a nucleic acid molecule encoding an polypeptide comprising an amino acid sequence that is identical to an amino acid sequence selected from SEQ ID NOs:26-41 except for the presence of no more than 2 amino acid substitutions.

This disclosure also includes nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the HER2 binding domain (e.g., a HER2 scFv) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
| --- | --- | --- |
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |

TABLE 1-continued

Examples of Spacers

| Name | Length | Sequence |
| --- | --- | --- |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48 aa | 48 aa | AKPTTTPAPRPPTPAPTIASQPLSLRPEACR PAAGGAVHTRGLDFACD (SEQ ID NO: 7) |
| CD8 hinge-45 aa | 45 aa | TTTPAPRPPTPAPTIASQPLSLRPEACR PAAGGAVHTRGLDFACD (SEQ ID NO: 8) |
| IgG4 (HL-CH3) (includes S228P in hinge) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFL YSRLTVDKSRWQEGNV FSCSVMHEALHNHYTQKSLSLSLGK SEQ ID NO: 9) |
| IgG4 (L235E, N297Q) | 229 aa | ESKYGPPCPSCPAPEFEGGPSVFLFPPK PKDTLMISRTPEVTCVVVDVSQEDPE VQFNWYVDGVEVHNAKTKPREEQFQ STYRVVSVLTVLHQDWLNGKEYKCK VSNKGLPSSIEKTISKAKGQPREPQVY TLPPSQEEMTKNQVSL TCLVKGFYPS DIAVEWESNGQPENNYKTTPPVLDSD GSFFLYSRLTVDKSRWQEGNVFSCSV MHEALHNHYTQKSLSLSLGK (SEQ ID NO: 10) |
| IgG4 (S228P, L235E, N297Q) | 229 aa | ESKYGPPCPPCPAPEFEGGPSVFLFPPK PKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSL TCLVKGFYPS DIAVEWESNGQPENNYKTTPPVLDSD GSFFLYSRLTVDKSRWQEGNVFSCSV MHEALHNHYTQKSLSLSLGK (SEQ ID NO: 11) |
| IgG4 (CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLSLGK (SEQ ID NO: 12) |
| HL | 22 aa | ESKYGPPCPPCPGGGSSGGGSG (SEQ ID NO: 42) |

Some spacer regions include all or part of an immunoglobulin (e.g., IgG 1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG 1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4(L235E, N297Q) spacer in Table 1 is 219 and the first amino acid in the IgG4(HL-CH3) spacer in Table 1 is 219 as is the first amino acid in the IgG hinge sequence and the IgG4 hinge linker (HL) sequence in Table 1

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234L, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 Proc Natl Acad Sci USA 63:78-85).

A variety of transmembrane domains can be used in the Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFIIFWV (SEQ ID NO: 14) |
| CD28 (M) | NM_006139 | 28 aa | MFWVLVVVGGVLACYSLLVTVAFIIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFF LTLRFSVV (SEQ ID NO: 20) |

Many of the CAR described herein include one or more (e.g., two) costimulatory domains. The costimulatory domain(s) are located between the transmembrane domain and the CD3ξ signaling domain. Table 3 includes examples of suitable costimulatory domains together with the sequence of the CD3ξ signaling domain.

TABLE 3

CD3 Domain and Examples of Costimulatory Domains

| Name | Accession | Length | Sequence |
|---|---|---|---|
| CD3ξ | 104132.1 | 113 aa | RVKFSRSADAPAYQQGQNQLYNELNLGR REEYDVLDKRRGRDPEMGGKPRRKNPQ EGLYNELQKDKMAEA YSEIGMKGERRR GKGHDGLYQGLSTATKDTYDALHMQAL PPR (SEQ ID NO: 21) |
| CD28 | NM 006139 | 42 aa | RSKRSRLLHSDYMNMTPRRPGPTRKHYQ PYAPPRDFAAYRS (SEQ ID NO: 22) |

TABLE 3-continued

CD3 Domain and Examples of Costimulatory Domains

| Name | Accession | Length | Sequence |
|------|-----------|--------|----------|
| CD28gg* | NM 006139 | 42 aa | RSKRSRGGQHSDYMNMTPRRPGPTRKHY QPYAPPRDFAAYRS (SEQ ID NO: 23) |
| 41BB | NM 001561 | 42 aa | KRGRKKLL YIFKQPFMRPVQTTQEEDG CSCRFPEEEEGGCEL (SEQ ID NO: 24) |
| OX40 | | 42 aa | ALYLLRRDQRLPPDAHKPPGGGSFRTPI QEEQADAHSTLAKI (SEQ ID NO: 25) |

DESCRIPTION OF DRAWINGS

FIG. 1 depicts the amino acid sequence of Her2scFv-IgG4(S228P, L235E,N297Q)-CD28tm-CD28gg-Zeta-T2A-CD19t (SEQ ID NO: 26). The various domains are listed in order below the sequence and are indicated by alternating underlining and non-underlining. The mature CAR sequence (SEQ ID NO: 34) does not include the GMCSFRa signal peptide, theT2A skip sequence or truncated CD19. Also called HER2(EQ)8ξ in FIGS. 3A-8E and throughout the specification.

FIG. 2 depicts the amino acid sequence of Her2scFv-IgG4(S228P,L235E,N297Q)-CD28tm-41BB-Zeta-T2A-CD19t (SEQ ID NO:27). The various domains are listed in order below the sequence and are indicated by alternating underlining and non-underlining. The mature CAR sequence (SEQ ID NO: 35) does not include the GMCSFRa signal peptide, theT2A skip sequence or truncated CD19. Also called HER2(EQ)BBξ in FIGS. 3A-8E and throughout the specification.

FIGS. 3A-D depict HER2-specific CAR constructs and CAR T cell expansion data.

FIGS. 4A-D depict in vitro characterization of HER2-CAR T cells against breast cancer cell lines.

FIGS. 8A-8D depict the results of studies on intraventrical delivery of HER2-CAR T cells.

FIG. 9 depicts the amino acid sequence of Her2scFv-CD8hinge-CD8tm-41BB-Zeta-T2A-CD19t (SEQ ID NO: 28). The various domains are listed in order below the sequence and are indicated by alternating underlining and non-underlining. The mature CAR sequence (SEQ ID NO: 36) does not include the GMCSFRa signal peptide, theT2A skip sequence or truncated CD 19.

FIG. 10 depicts the amino acid sequence of Her2scFv-IgG4hinge(S228P)-linker-CD8tm-41BB-Zeta-T2A-CD19t. (SEQ ID NO:29) The various domains are listed in order below the sequence and are indicated by alternating underlining and non-underlining. The mature CAR sequence (SEQ ID NO: 37) does not include the GMCSFRa signal peptide, theT2A skip sequence or truncated CD 19.

FIG. 11 depicts the amino acid sequence of Her2scFv-IgG4(S228P)-Linker-IgG4 CH3-CD8tm-41BB-Zeta-T2A-CD19t (SEQ ID NO: 30). The various domains are listed in order below the sequence and are indicated by alternating underlining and non-underlining. The mature CAR sequence (SEQ ID NO: 38) does not include the GMCSFRA signal peptide, theT2A skip sequence or truncated CD19.

FIG. 12 depicts the amino acid sequence of Her2scFv-IgG4(S228P)-Linker-IgG4 CH3-CD28tm-CD28gg-Zeta-T2A-CD19t (SEQ ID NO: 31). The various domains are listed in order below the sequence and are indicated by alternating underlining and non-underlining. The mature CAR sequence (SEQ ID NO: 39) does not include the GMCSFRa signal peptide, theT2A skip sequence or truncated CD19.

FIG. 13 depicts the amino acid sequence of Her2scFv-Linker-CD28tm-CD28gg-Zeta-T2A-CD19t (SEQ ID NO: 32). The various domains are listed in order below the sequence and are indicated by alternating underlining and non-underlining. The mature CAR sequence (SEQ ID NO: 40) does not include the GMCSFRa signal peptide, theT2A skip sequence or truncated CD19.

FIG. 14 depicts the amino acid sequence of Her2scFv-Linker-CD8tm-41BB-Zeta-T2A-CD19t. (SEQ ID NO: 33). The various domains are listed in order below the sequence and are indicated by alternating underlining and non-underlining. The mature CAR sequence (SEQ ID NO: 41) does not include the GMCSFRa signal peptide, theT2A skip sequence or truncated CD19.

FIGS. 16A-16C show the results of studies examining CD107a and INF gamma produced when TCM expressing the varios CAAR are exposed to cells not expressing HER2 (MDA-MB-468), low HER2 (231BR), low HER2 (231BRHER2LO) or high HER2 (231BRHER2HI).

DETAILED DESCRIPTION

Figure 5A:
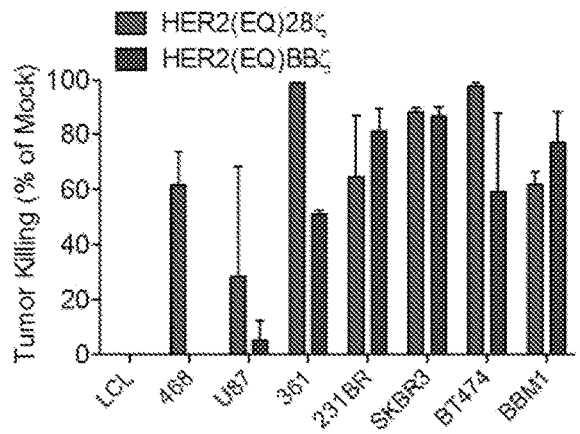
FIGS. 5A-5F depict the result of studies on the in vitro tumor activity of HER2-CAR T cells.

Described below is the structure, construction and characterization of various chimeric antigen receptors targeting HER2 and useful in treating HER2-expressing breast cancer as well as breast to brain metastasis. Importantly, the CAR described herein can be used in ACT to treat HER2 expressing tumors in the brain by intraventricular or intratumoral delivery.

A chimeric antigen (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

In some cases the CAR described herein can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD 19t provides a marker for immunological targeting of the transduced cells in vivo using clinically available antibodies and/or immunotoxin reagents to selectively delete the therapeutic cells, and thereby functioning as a suicide switch.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets or $T_{CM}$ or $T_{CM/SCM/N}$ can be transduced with a vector for CAR expression. Central memory T cells are one useful T cell subset. Central memory T cell can be isolated from peripheral blood mononuclear cells (PBMC) by enriching for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a SIN lentiviral vector that directs the expression of the CAR as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Structure of Two HER2-CAR

One CAR comprising a HER2 scFv described herein is referred to as Her2scFv-IgG4(L235E, N297Q)-CD28tm-CD28gg-Zeta-T2A-CD19t. This CAR includes a variety of important features including: a scFv targeted to HER2; an IgG4 Fc region that is mutated at two sites within the CH2 region (L235E; N297Q) in a manner that reduces binding by Fc receptors (FcRs); a CD28 transmembrane domain, a CD28 co-stimulatory domain, and CD3ξ activation domain. FIG. 1 presents the amino acid sequence of this CAR, including the sequence of the truncated CDI9 sequence used for monitoring CAR expression and the T2A ribosomal skip sequence that allows the CAR to be produced without fusion of the truncated CDI9 sequence. As shown in FIG. 2, the immature CAR includes: GMCSFR signal peptide, HER2 scFv, IgG4 that acts as a spacer, a CD8 transmembrane domain, a 4-IBB co-stimulatory domain that includes a LL to GG sequence alteration, a three Gly sequence, CD3 Zeta stimulatory domain. The transcript also encodes a T2A ribosomal sequence and a truncated CDI9 sequence that are not part of the CAR protein sequence. The mature CAR is identical to the immature CAR, but lacks the GMCSF signal peptide.

Example 2: Construction and Structure of epHIV7 Used for Expression of HER2-Specific CAR T Cells The epHIV7 vector is a vector that can used for expression of the HER2-specific CAR. Is was produced from pHIV7 vector. Importantly, this vector uses the human EFI promoter to drive expression of the CAR. Both the 5' and 3' sequences of the vector were derived from pv653RSN as previously derived from the HXBc2 provirus. The polypurine tract DNA flap sequences (cPPT) were derived from HIV-I strain pNL4-3 from the NIH AIDS Reagent Repository. The woodchuck post-transcriptional regulatory element (WPRE) sequence was previously described.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step I, the sequences from 5' LTR to rev-responsive element (RRE) made p5'HIV-I 5I, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-I pNL4-3 (55) was amplified from pNL4-3 and placed between the RRE and the WPRE sequences in pHIV 6 to make pHIV-7. This parent plasmid pHIV7-GFP (GFP, green fluorescent protein) was used to package the parent vector using a four-plasmid system.

A packaging signal, psi (ψ), is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector, are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EFIα-HTLV promoter (EFIp), and the new plasmid was named epHIV7. The EFIp has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes.

Example 3: Production of Vectors for Transduction of Patient T Cells

Vectors for transduction of patient T cells can be prepared as follows. For each plasmid the plasmid expressing the CAR and, optionally, a marker such as truncated CD19; 2) pCgp; 3) pCMV-G; and 4) pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells are expanded from the 293T working cell (WCB), which has been tested to confirm sterility and the absence of viral contamination. A vial of 293T cells from the 293T WCB is thawed. Cells are grown and expanded until sufficient numbers of cells exists to plate an appropriate number of 10 layer cell factories (CFs) for vector production and cell train maintenance. A single train of cells can be used for production.

The lentiviral vector is produced in sub-batches of up to 10 CFs. Two sub-batches can be produced in the same week leading to the production of approximately 20 L of lentiviral supernatant/week. The material produced from all sub-batches is pooled during the downstream processing phase, in order to produce one lot of product. 293T cells are plated in CFs in 293T medium (DMEM with 10% FBS). Factories are placed in a 37° C. incubator and horizontally leveled in order to get an even distribution of the cells on all the layers of the CF. Two days later, cells are transfected with the four lentiviral plasmids described above using the CaPO4 method, which involves a mixture of Tris:EDTA, 2M CaCl, 2xHBS, and the four DNA plasmids. Day 3 after transfection, the supernatant containing secreted lentiviral vectors is collected, purified and concentrated. After the supernatant is removed from the CFs, End-of-Production Cells are collected from each CF. Cells are trypsinized from each factory and collected by centrifugation. Cells are resuspended in freezing medium and cryopreserved. These cells are later used for replication-competent lentivirus (RCL) testing.

To purify and formulate vectors crude, supernatant is clarified by membrane filtration to remove the cell debris. The host cell DNA and residual plasmid DNA are degraded by endonuclease digestion (Benzonase®). The viral supernatant is clarified of cellular debris using a 0.45 μm filter. The clarified supernatant is collected into a pre-weighed container into which the Benzonase® is added (final concentration 50 U/mL). The endonuclease digestion for residual plasmid DNA and host genomic DNA is performed at 37° C. for 6 h. The initial tangential flow ultrafiltration (TFF) concentration of the endonuclease-treated supernatant is used to remove residual low molecular weight components from the crude supernatant, while concentrating the virus ~20 fold. The clarified endonuclease-treated viral supernatant is circulated through a hollow fiber cartridge with a NMWCO of 500 kD at a flow rate designed to maintain the shear rate at ~4,000 sec$^{-1}$ or less, while maximizing the flux rate. Diafiltration of the nuclease-treated supernatant is initiated during the concentration process to sustain the cartridge performance. An 80% permeate replacement rate is established, using 4% lactose in PBS as the diafiltration buffer. The viral supernatant is brought to the target volume, representing a 20-fold concentration of the crude supernatant, and the diafiltration is continued for 4 additional exchange volumes, with the permeate replacement rate at 100%.

Further concentration of the viral product is accomplished by using a high speed centrifugation technique. Each sub-batch of the lentivirus is pelleted using a Sorvall RC-26 plus centrifuge at 6000 RPM (6,088 RCF) at 6° C. for 16-20 h. The viral pellet from each sub-batch is then reconstituted in a 50 mL volume with 4% lactose in PBS. The reconstituted pellet in this buffer represents the final formulation for the virus preparation. The entire vector concentration process results in a 200-fold volume reduction, approximately. Following the completion of all of the sub-batches, the material is then placed at −80° C., while samples from each sub-batch are tested for sterility. Following confirmation of sample sterility, the sub-batches are rapidly thawed at 37° C. with frequent agitation. The material is then pooled and manually aliquoted in the Class II Type A/B3 biosafety cabinet. A fill configuration of 1 mL of the concentrated lentivirus in sterile USP class 6, externally threaded O-ring cryovials is used.

To ensure the purity of the lentiviral vector preparation, it is tested for residual host DNA contaminants, and the transfer of residual host and plasmid DNA. Among other tests, vector identity is evaluated by RT-PCR to ensure that the correct vector is present.

Example 4: Preparation of T Cells Suitable for Use in ACT

If $T_{CM}$ are to be used to express the CAR, suitable patient cells can be prepared as follows. First, T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anti-cancer therapy.

Suitable TcM can be generated as follow. Apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the Clini-MACS™ separation device. Following depletion, negative fraction cells are enriched for CD62L+ $T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with lentiviral vector expressing the desired CAR at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Example 5: Expression of CAR Targeted to HER2

FIG. 3A is a schematic diagram of two the HER2-specific CAR constructs depicted in FIG. 1 and FIG. 2. In HER2 (EQ)28ξ the scFv is tethered to the membrane by a modified IgG4 Fc linker (double mutant, L235E; N297Q), containing a CD28 transmembrane domain, an intracellular CD28 co-stimulatory domain and a cytolytic CD3ξ domain. The T2A skip sequence separates the CAR from a truncated CD19 (CD19t) protein employed for cell tracking. HER2 (EQ)BBξ is similar except that the costimulatory domain is 4-1BB rather than CD28 and the transmembrane domain is a CD8 transmembrane domain rather than a CD28 transmembrane domain. Human central memory (TCM) cells were transfected with a lentiviral vector expressing either HER2(EQ)28ξ or HER2(EQ)BBξ. FIG. 3B depicts representative FACS data of human TCM surface phenotype. FIG. 3C depicts the results of assays for CD 19 and Protein L expression in TCM transfected with a lentiviral vector expressing either HER2(EQ)28ξ or HER2(EQ)BBξ. As can be seen from these results, transfection efficiency as assessed by CD19 expression was similar for both CAR. However, Protein L expression was lower for HER2(EQ)BBξ than for HER2(EQ)28ξ suggesting that the HER2(EQ)BBξ CAR is less stable that the HER2(EQ)BBξ. Analysis of cell expansion (FIG. 3D) shows that neither CAR interferes with T cell expansion.

Example 6: In Vitro Characterization of HER2-CAR T Cells Against Various Breast Cancer Cell Lines A variety of breast cancer cell lines, including, HER2-negative lines (LCL lymphoma, MDA-MB-468, U87 glioma), low-HER2 expressing lines (MDA-MB-361, 231BR) and high-HER2 expressing lines (SKBR3, BT474, BBM1) were used to characterize HER2(EQ)28 and HER2 (EQ)BBξ. FIG. 4A depicts the HER2 expression level of each of these lines. Flow cytometry (gated on CAR+ T cells) was used to characterize CD107a degranulation and IFNy production in Mock (untransduced), HER2(EQ)28ξ or HER2(EQ)BBξ CAR T cells following a 5 hr co-culture with either MDA-MB-361 tumor cells (low HER2 expressing) or BBM1 tumor cells (high HER2 expressing). The results of this analysis are presented in FIG. 4B. Similar studies were conducted with the other breast cancer cells lines, and the results are summarized in FIG. 4C. Production of IFNy production by HER2-CAR T cells following a 24 hr culture with recombinant HER2 protein or tumor targets was measured by ELISA and the results of this analysis are shown in FIG. 4D.

Example 7: In Vitro Anti-Tumor Activity

Figure 5B:
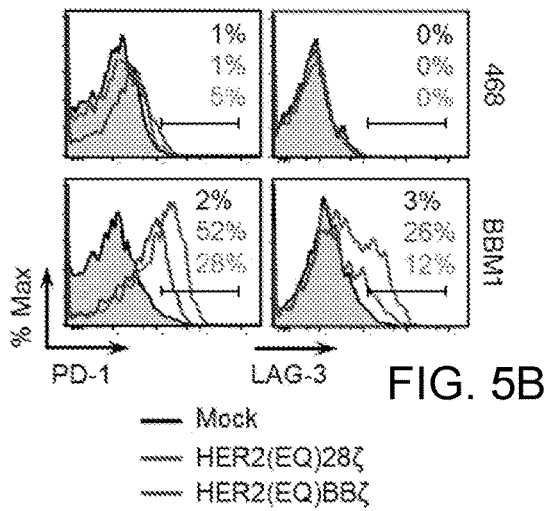
Figure 5C:
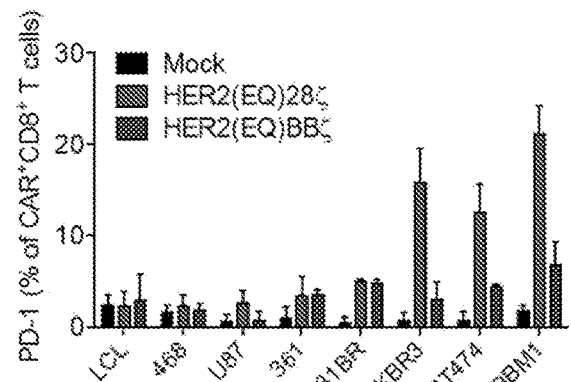
Figure 5D:
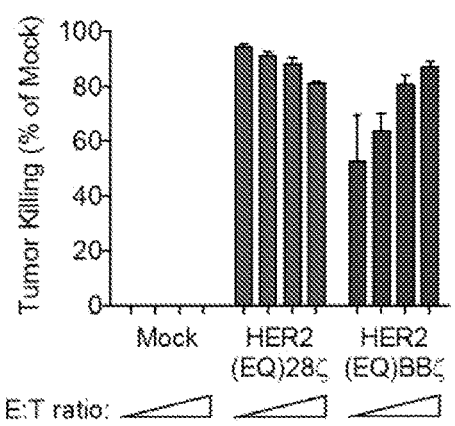
Figure 5E:
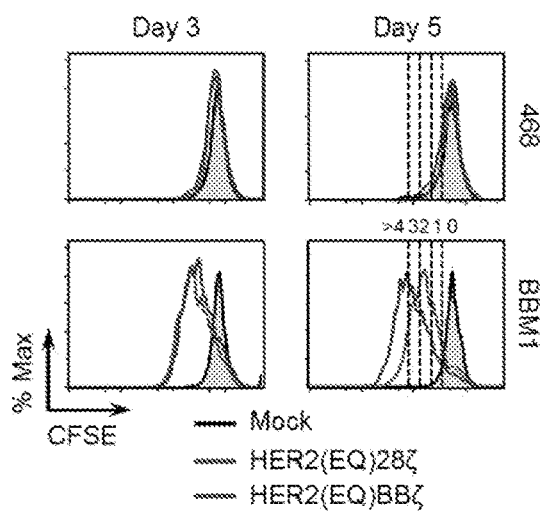
Figure 5F:
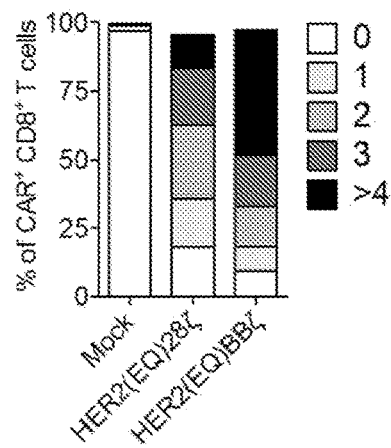

Flow cytometry was used to assess tumor cell killing following a 72h co-culture of Mock (untransduced), HER2 (EQ)28ξ or HER2(EQ)BBξ CAR T cells with tumor targets. The results of this analysis are presented in FIG. 5A. PD-1 and LAG-3 induction in total CAR T cells after a 72h co-culture with HER2-negative MDA-MB-468 or HER2-positive BBM1 cells was measured, and the results of this analysis are presented in FIG. 5B. PD-1 induction in CD8+ CAR T cells following a 72h co-culture with tumor targets that are HER2-negative (LCL lymphoma, MDA-MB-468, U87 glioma), low-HER2 expressing (MDA-MB-361, 231BR) or high-HER2 expressing (SKBR3, BT474, BBM 1) was measured, and the results of this analysis are presented in FIG. 5C. These studies suggest that HER2(EQ) BBξ causes lower PD-1 induction that does HER2(EQ)28ξ. Tumor cell killing with Effector:Tumor (E:T) ratio ranging from 0.25:1 to 2:1 was measured for both HER2(EQ)28ξ or HER2(EQ)BBξ CAR T cells. The results of this analysis are presented in FIG. 5D, which shows that both HER2(EQ)28ξ and HER2(EQ)BBξ are effective in tumor cell killing in vitro. CFSE proliferation of HER2-CAR T cells following a 72h co-culture with MDA-MB-468 or BBMI cells was measured by flow cytometry. The results of this analysis are presented in FIG. 5E, which shows that HER2(EQ)BBξ CAR T cells proliferate more than HER2(EQ)28ξ CAR T cells.

Example 8: In Vivo Anti-Tumor Activity

Figures 6A, 6B, 6C, 6D, 6E, 6F, 6G, 6H, 6I:
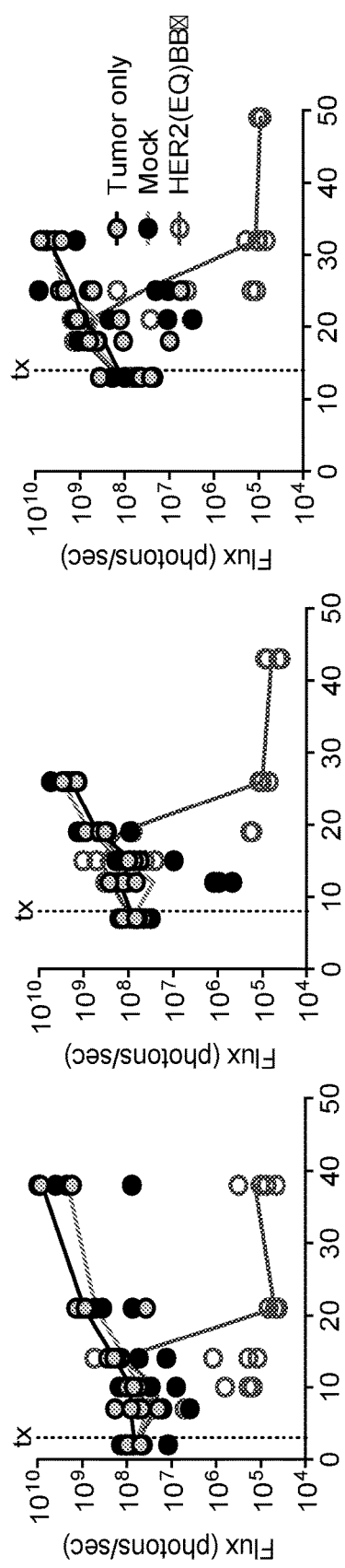
FIGS. 6A-6I depict the result of studies on the in vivo anti-tumor efficacy of local intratumorally-delivered HER2-CAR T cells.

The activity of intratumorally delivered HER2 CAR T cells was assessed in a patient-derived breast-to-brain metastasis model. FIGS. 6A-6C are H&E staining of tumors. Mice were treating by injection directly into the tumor with Mock (untransduced) or HER2(EQ)BBξ CAR T cells. FIGS. 6D-6F depict the results of optical imaging of the tumors and FIGS. 6G-6I are Kaplan-Meier survival curves for mice treated locally with either at day 3, 8 or 14 post tumor injection. These studies show that HER2(EQ)BBξ CAR T cells have potent anti-tumor efficacy in vivo when injected directly into the tumor.

Figure 7A:
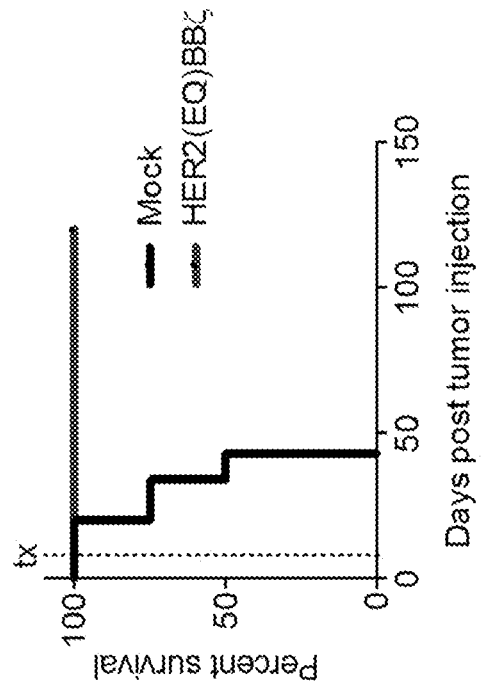
FIGS. 7A-7D depict the results of studies on local delivery of HER2-CAR T cells in human orthotopic BBM xenograft models.
Figure 7B:
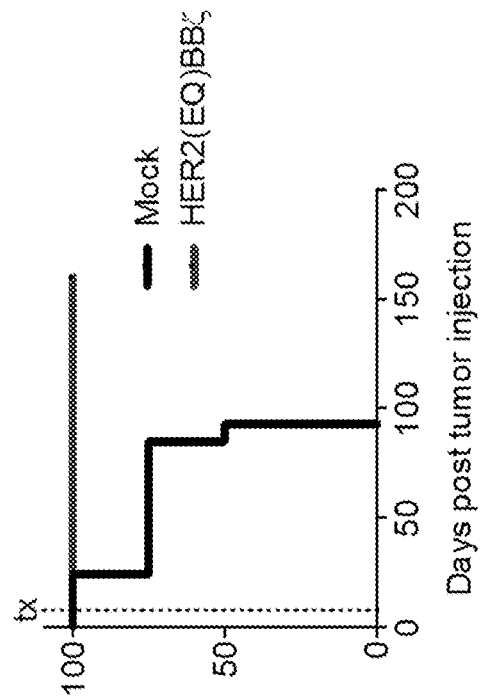
Figure 7C:
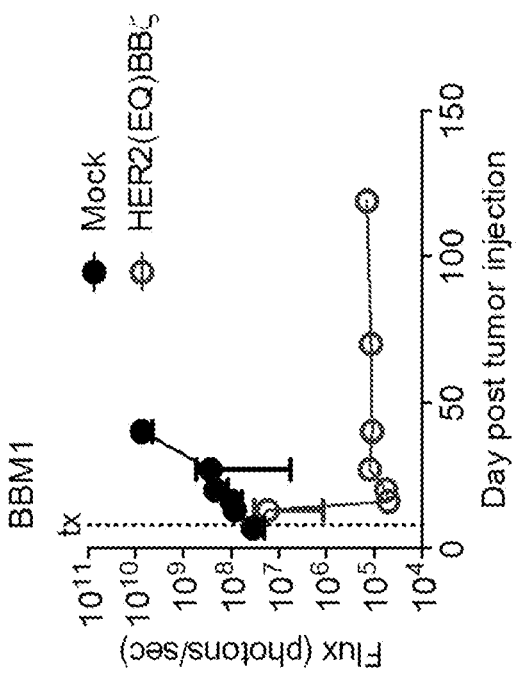
Figure 7D:
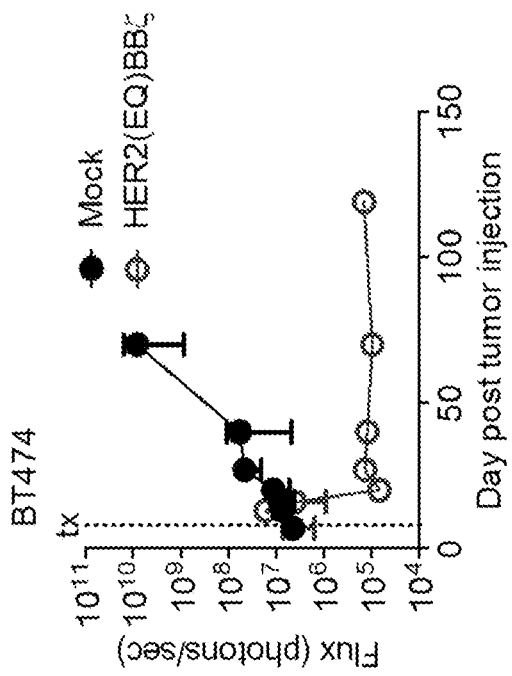

To assess anti-tumor efficacy in human xenograft models of breast-to-brain metastasis, BBM1 cells (0.2M) or BT474 (0.15M) were intracranially injected in NSG mice. At day 8 post tumor injection, HER2(EQ)28ξ or HER2(EQ)BBξ, or Mock (untransduced) T cells (IM) were injected intratumorally. BBMI (FIG. 7A) and BT474 (FIG. 7B) tumors were monitored by luciferase-based optical imaging. Kaplan Meier curves are presented in FIG. 7C and FIG. 7D.

A human patient-derived orthotopic xenograft model of breast-to-brain metastasis was also used to assess HER2 (EQ)28ξ and HER2(EQ)BBξ CAR T cells. FIG. 8A illustrates the region of tumor implantation by stereotactic injection of BBM1 cells (0.2M), and intraventricular T cell delivery. Staining of tumors is depicted in FIG. 8B. At day 14 post tumor injection, HER2(EQ)28ξ, HER2(EQ)BBξ, or Mock (untransduced) T cells (0.5M) were injected intratumorally. Tumor growth was monitored by luciferase-based optical imaging. FIG. 8C presents the flux averages for each treatment group, and FIG. 8D presents the Kaplan Meier survival curve for each treatment group.

Example 9: Additional CAR Targeted to HER2

FIGS. 9-14 depict the amino acid sequences of a various CAR having different linkers. Specifically, the CAR differ in the sequence and length of the portion between the HER2 targeted scFv and the transmembrane domain. The transmembrane domain is CD8, CD28 or CD28gg. The co-stimulatory domain is 4-1BB or CD28. All have a CD3ζ stimulatory domain. In each case a T2A skip sequence separates the CAR from a truncated CD19 (CD19t) protein employed for cell tracking.

Figure 15A:
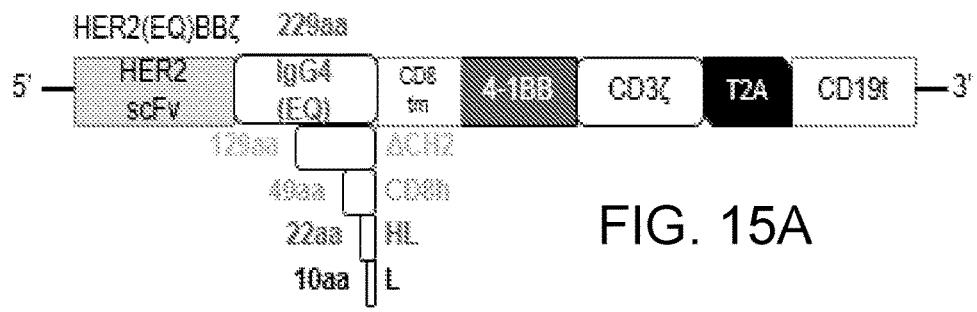
FIGS. 15A-15C depict the results of studies characterizing certain additional CAR with various spacers. The IgG3 (EQ) is in FIG. 2; DeltaCh2 is in FIG. 11; CD8h is in FIG. 9; HL is in FIG. 10; and L is in FIG. 14.
Figure 15B:
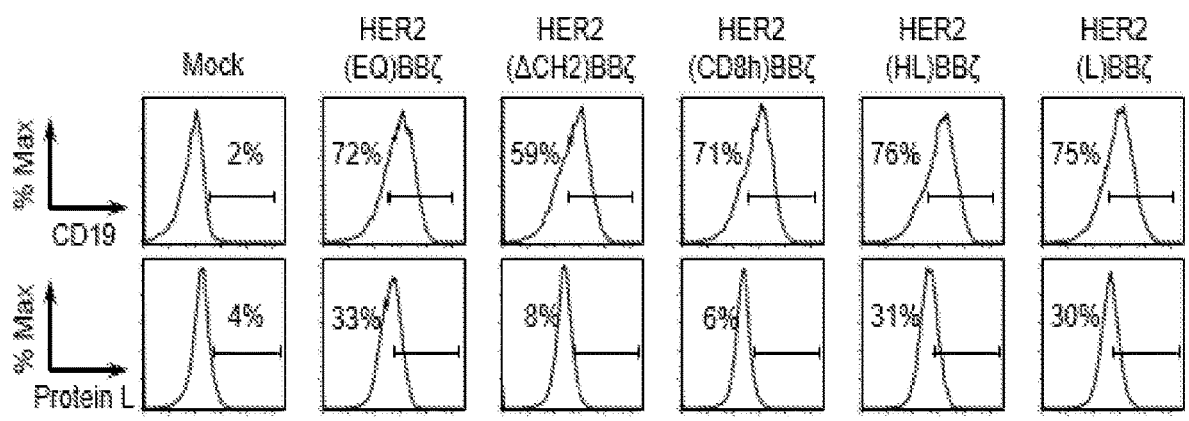
Figure 15C:
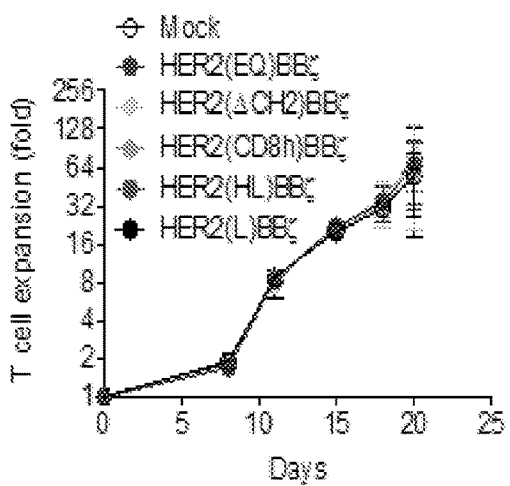
Figure 17A:
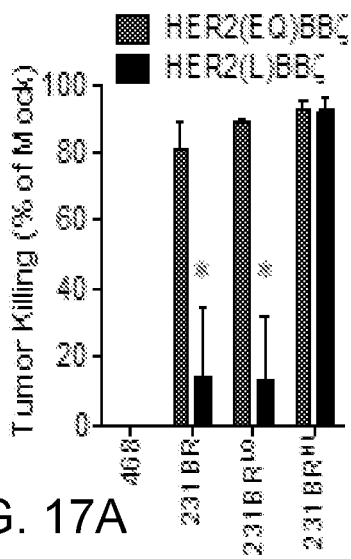
FIGS. 17A-17D show the results of studies examining PD-1 production and tumor cell killing ins various cell lines with the CAR of FIG. 2 (HER2(EQ)BBξ or FIG. 14 (HER2 (L)BBξ).
Figure 17B:
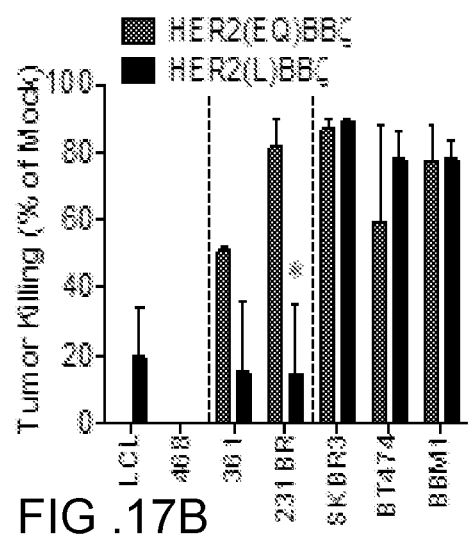
Figure 17C:
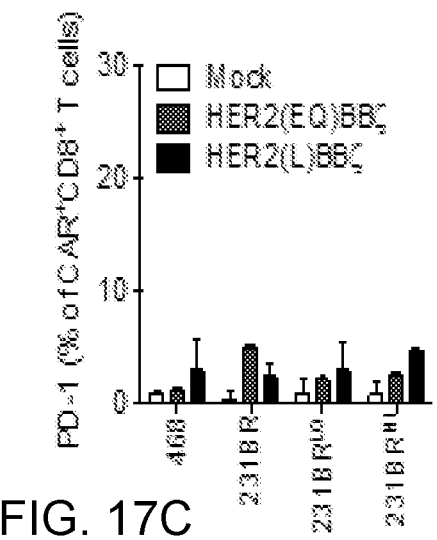
Figure 17D:
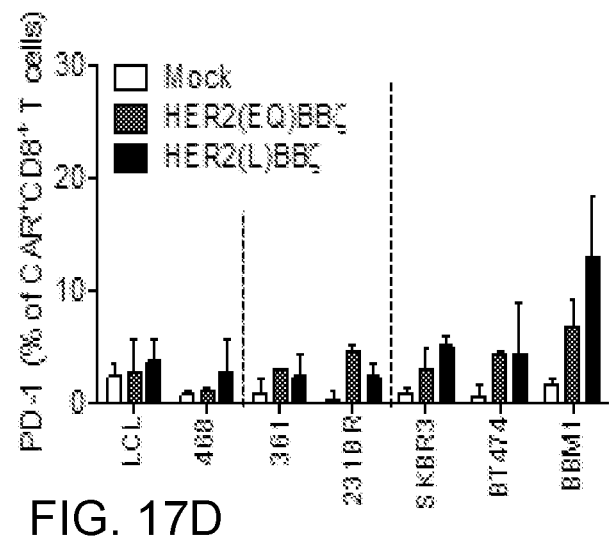
Figure 18A:
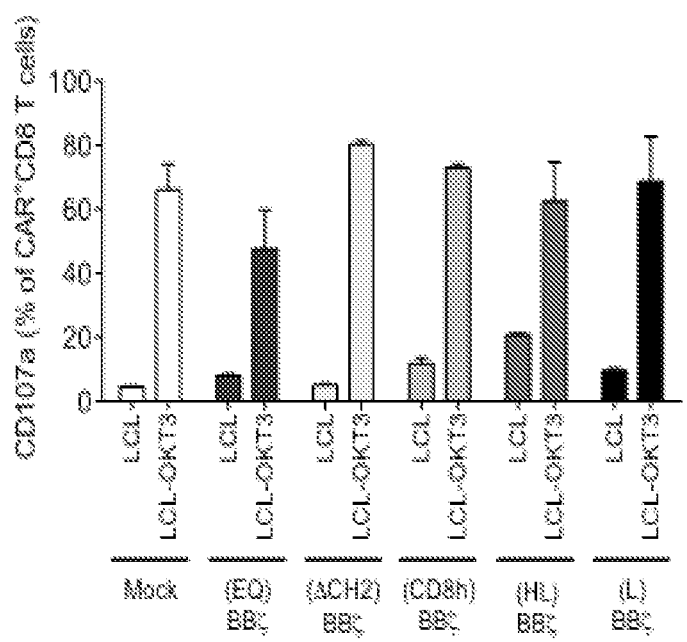
FIGS. 18A-18B show the results of studies examining CD107a and INF gamma produced when TCM expressing the varios CAAR are exposed to cells not expressing HER2 (MDA-MB-468), low HER2 (231BR), low HER2 (231BRHER2LO) or high HER2 (231BRHER2HI).
Figure 18B:
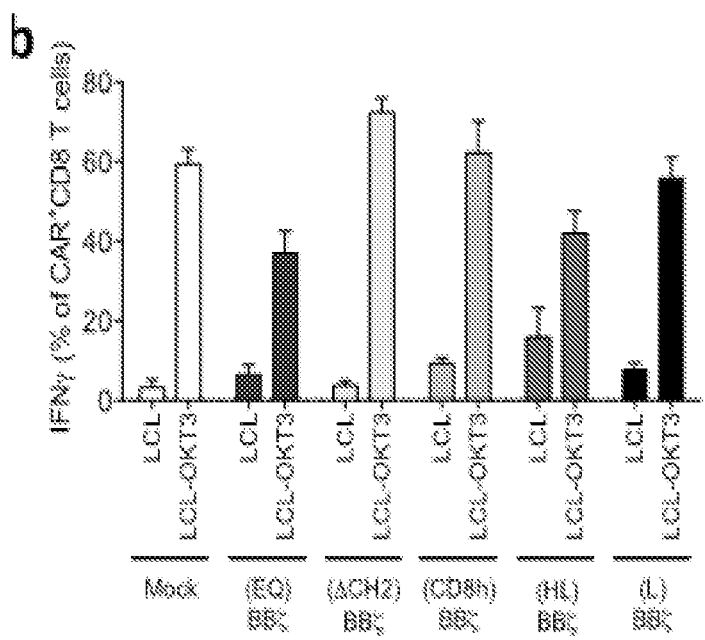

FIG. 15A schematically depicts various HER2 CAR that are identical except for the sequence and length of the portion between the HER2 scFv and the CD8 transmembrane domain. All include a 4-1BB co-stimulatory domain followed by a CD3ζ stimulatory domain. FIG. 15B depicts the results of assays for CD19 and Protein L expression in $T_{CM}$ transfected with a lentiviral vector expressing the indicated CAR. As can be seen from these results, transfection efficiency as assessed by CD19 expression was similar for both CAR. However, Protein L expression was lower for HER2(EQ)BBξ than for HER2(EQ)BBζ suggesting that the HER2(EQ)BBζ CAR is less stable that the HER2(EQ)BBζ. Analysis of cell expansion (FIG. 15C) shows that none of the CAR interfere with T cell expansion. FIGS. 16-18 show the results of additional studies showing that a CAR with a very short spacer (FIG. 14) is relatively selective for CAR expressing high levels of HER2. Such CAR may be useful in treating HER2 expressing cancers where it is desirable to spare cells expressing a lower level of HER2 than the cancerous cells.

What is claimed is:

1. A nucleic acid molecule encoding a chimeric antigen receptor, wherein the chimeric antigen receptor comprises the amino acid sequence of any of SEQ ID NOs: 34-41.

2. An isolated population of human T cells transduced by a vector comprising an expression cassette encoding a chimeric antigen receptor, wherein the chimeric antigen receptor comprises the amino acid sequence of any of SEQ ID NOs: 34-41.

3. A method of treating a HER2 expressing brain cancer in a patient comprising administering a population of autologous or allogeneic human T cells transduced by a vector comprising an expression cassette encoding a chimeric antigen receptor, wherein chimeric antigen receptor comprises an amino acid sequence selected from SEQ ID NOs:34-41.

4. The method of claim 3 wherein the population of human T cells comprise CD62L+ memory T cells.

5. The method claim 3 wherein the cancer is a breast to brain metastasis.

6. The method of claim 3, wherein the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs:34-41.

7. The method of claim 3 wherein the T cells are administered intratumorally.

8. The method of claim 3 wherein the T cells are administered intraventricularly.

9. The method of claim 3 wherein the T cells are administered intravetricularly adjacent to a tumor.

10. An isolated T cell expressing a polypeptide or a chimeric antigen receptor comprising an amino acid sequence that is identical to an amino acid sequence selected from SEQ ID NOs:26-41.

11. The nucleic acid molecule of claim 1, wherein the chimeric antigen receptor comprises the amino acid sequence of SEQ ID NO: 34.

12. The nucleic acid molecule of claim 1, wherein the chimeric antigen receptor comprises the amino acid sequence of SEQ ID NO: 35.

13. The nucleic acid molecule of claim 1, wherein the chimeric antigen receptor comprises the amino acid sequence of SEQ ID NO: 36.

14. The nucleic acid molecule of claim 1, wherein the chimeric antigen receptor comprises the amino acid sequence of SEQ ID NO: 37.

15. The nucleic acid molecule of claim 1, wherein the chimeric antigen receptor comprises the amino acid sequence of SEQ ID NO: 38.

16. The nucleic acid molecule of claim 1, wherein the chimeric antigen receptor comprises the amino acid sequence of SEQ ID NO: 39.

17. The nucleic acid molecule of claim 1, wherein the chimeric antigen receptor comprises the amino acid sequence of SEQ ID NO: 40.

18. The nucleic acid molecule of claim 1, wherein the chimeric antigen receptor comprises the amino acid sequence of SEQ ID NO: 41.

19. A nucleic acid molecule encoding a polypeptide, wherein the polypeptide comprises the amino acid sequence of any of SEQ ID NOs: 26-33.

20. The nucleic acid molecule of claim 19, wherein the polypeptide comprises the amino acid sequence of SEQ ID NO: 26.

21. The nucleic acid molecule of claim 19, wherein the polypeptide comprises the amino acid sequence of SEQ ID NO: 27.

22. The nucleic acid molecule of claim 19, wherein the polypeptide comprises the amino acid sequence of SEQ ID NO: 28.

23. The nucleic acid molecule of claim 19, wherein the polypeptide comprises the amino acid sequence of SEQ ID NO: 29.

24. The nucleic acid molecule of claim 19, wherein the polypeptide comprises the amino acid sequence of SEQ ID NO: 30.

25. The nucleic acid molecule of claim 19, wherein the polypeptide comprises the amino acid sequence of SEQ ID NO: 31.

26. The nucleic acid molecule of claim 19, wherein the polypeptide comprises the amino acid sequence of SEQ ID NO: 32.

27. The nucleic acid molecule of claim 19, wherein the polypeptide comprises the amino acid sequence of SEQ ID NO: 33.

28. An isolated population of human T cells transduced by a vector comprising an expression cassette encoding a polypeptide, wherein the polypeptide comprises the amino acid sequence of any of SEQ ID NOs: 26-33.

29. The isolated population of human T cells of claim 28, wherein the polypeptide comprises the amino acid sequence of SEQ ID NO: 26.

30. The isolated population of human T cells of claim 28, wherein the polypeptide comprises the amino acid sequence of SEQ ID NO: 27.

31. The isolated population of human T cells of claim 28, wherein the polypeptide comprises the amino acid sequence of SEQ ID NO: 28.

32. The isolated population of human T cells of claim 28, wherein the polypeptide comprises the amino acid sequence of SEQ ID NO: 29.

33. The isolated population of human T cells of claim 28, wherein the polypeptide comprises the amino acid sequence of SEQ ID NO: 30.

34. The isolated population of human T cells of claim 28, wherein the polypeptide comprises the amino acid sequence of SEQ ID NO: 31.

35. The isolated population of human T cells of claim 28, wherein the polypeptide comprises the amino acid sequence of SEQ ID NO: 32.

36. The isolated population of human T cells of claim 28, wherein the polypeptide comprises the amino acid sequence of SEQ ID NO: 33.

37. The isolated population of human T cells of claim 18, wherein the chimeric antigen receptor comprises the amino acid sequence of SEQ ID NO: 34.

38. The isolated population of human T cells of claim 18, wherein the chimeric antigen receptor comprises the amino acid sequence of SEQ ID NO: 35.

39. The isolated population of human T cells of claim 18, wherein the chimeric antigen receptor comprises the amino acid sequence of SEQ ID NO: 36.

40. The isolated population of human T cells of claim 18, wherein the chimeric antigen receptor comprises the amino acid sequence of SEQ ID NO: 37.

41. The isolated population of human T cells of claim 18, wherein the chimeric antigen receptor comprises the amino acid sequence of SEQ ID NO: 38.

42. The isolated population of human T cells of claim 18, wherein the chimeric antigen receptor comprises the amino acid sequence of SEQ ID NO: 39.

43. The isolated population of human T cells of claim 18, wherein the chimeric antigen receptor comprises the amino acid sequence of SEQ ID NO: 40.

44. The isolated population of human T cells of claim 18, wherein the chimeric antigen receptor comprises the amino acid sequence of SEQ ID NO: 41.

45. The isolated T cell of claim 10, wherein the polypeptide or chimeric antigen receptor comprises an amino acid sequence that is identical to SEQ ID NO:26.

46. The isolated T cell of claim 10, wherein the polypeptide or chimeric antigen receptor comprises an amino acid sequence that is identical to SEQ ID NO:27.

47. The isolated T cell of claim 10, wherein the polypeptide or chimeric antigen receptor comprises an amino acid sequence that is identical to SEQ ID NO: 28.

48. The isolated T cell of claim 10, wherein the polypeptide or chimeric antigen receptor comprises an amino acid sequence that is identical to SEQ ID NO: 29.

49. The isolated T cell of claim 10, wherein the polypeptide or chimeric antigen receptor comprises an amino acid sequence that is identical to SEQ ID NO: 30.

50. The isolated T cell of claim 10, wherein the polypeptide or chimeric antigen receptor comprises an amino acid sequence that is identical to SEQ ID NO: 31.

51. The isolated T cell of claim 10, wherein the polypeptide or chimeric antigen receptor comprises an amino acid sequence that is identical to SEQ ID NO: 32.

52. The isolated T cell of claim 10, wherein the polypeptide or chimeric antigen receptor comprises an amino acid sequence that is identical to SEQ ID NO: 33.

53. The isolated T cell of claim 10, wherein the polypeptide or chimeric antigen receptor comprises an amino acid sequence that is identical to SEQ ID NO:34.

54. The isolated T cell of claim 10, wherein the polypeptide or chimeric antigen receptor comprises an amino acid sequence that is identical to SEQ ID NO:35.

55. The isolated T cell of claim 10, wherein the polypeptide or chimeric antigen receptor comprises an amino acid sequence that is identical to SEQ ID NO: 36.

56. The isolated T cell of claim 10, wherein the polypeptide or chimeric antigen receptor comprises an amino acid sequence that is identical to SEQ ID NO: 37.

57. The isolated T cell of claim 10, wherein the polypeptide or chimeric antigen receptor comprises an amino acid sequence that is identical to SEQ ID NO: 38.

58. The isolated T cell of claim 10, wherein the polypeptide or chimeric antigen receptor comprises an amino acid sequence that is identical to SEQ ID NO: 39.

59. The isolated T cell of claim 10, wherein the polypeptide or chimeric antigen receptor comprises an amino acid sequence that is identical to SEQ ID NO: 40.

60. The isolated T cell of claim 10, wherein the polypeptide or chimeric antigen receptor comprises an amino acid sequence that is identical to SEQ ID NO: 41.

* * * * *

UNITED STATES PATENT AND TRADEMARK OFFICE
CERTIFICATE OF CORRECTION

PATENT NO. : 11,197,919 B2
APPLICATION NO. : 15/773754
DATED : December 14, 2021
INVENTOR(S) : Saul J. Priceman, Stephen J. Forman and Christine E. Brown It is certified that error appears in the above-identified patent and that said Letters Patent is hereby corrected as shown below:

In the Claims

Column 91, Line 33, Claim 5, delete "method" and insert -- method of --

Column 91, Line 48, Claim 9, delete "intravetricularly" and insert -- intraventricularly --

Column 93, Line 13, Claim 37, delete "claim 18," and insert -- claim 2, --

Column 93, Line 16, Claim 38, delete "claim 18," and insert -- claim 2, --

Column 93, Line 19, Claim 39, delete "claim 18," and insert -- claim 2, --

Column 93, Line 22, Claim 40, delete "claim 18," and insert -- claim 2, --

Column 93, Line 25, Claim 41, delete "claim 18," and insert -- claim 2, --

Column 93, Line 28, Claim 42, delete "claim 18," and insert -- claim 2, --

Column 93, Line 31, Claim 43, delete "claim 18," and insert -- claim 2, --

Column 93, Line 34, Claim 44, delete "claim 18," and insert -- claim 2, --

Signed and Sealed this
Third Day of October, 2023

Katherine Kelly Vidal
*Director of the United States Patent and Trademark Office*